(12) United States Patent
Persson et al.

(10) Patent No.: US 9,066,947 B2
(45) Date of Patent: *Jun. 30, 2015

(54) INDOLYL-SUBSTITUTED PYRAZINO[1,2-B]ISOQUINOLINES FOR CANCER TREATMENT

(71) Applicant: Everest Biosciences, Inc., Sunnyvale, CA (US)

(72) Inventors: Jenny Persson, Malmo (SE); Rikard Larsson, Tagarp (SE); Olov Sterner, Malmo (SE); Martin Johansson, Limhamn (SE)

(73) Assignee: EVEREST BIOSCIENCES, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/263,886

(22) Filed: Apr. 28, 2014

(65) Prior Publication Data

US 2014/0235644 A1    Aug. 21, 2014

Related U.S. Application Data

(63) Continuation of application No. 13/379,497, filed as application No. PCT/GB2010/000514 on Mar. 19, 2010, now Pat. No. 8,754,086, which is a continuation of application No. PCT/GB2009/001598, filed on Jun. 25, 2009.

(51) Int. Cl.
| *A61K 31/498* | (2006.01) |
| *C07D 487/14* | (2006.01) |
| *A61K 31/4985* | (2006.01) |
| *C07D 471/04* | (2006.01) |
| *C07D 491/14* | (2006.01) |
| *C07D 471/14* | (2006.01) |

(52) U.S. Cl.
CPC .......... *A61K 31/4985* (2013.01); *C07D 471/04* (2013.01); *C07D 491/14* (2013.01); *C07D 471/14* (2013.01)

(58) Field of Classification Search
CPC ............................ A61K 31/498; C07D 487/14
USPC ..................... 514/250; 544/344; 548/464
See application file for complete search history.

(56) References Cited

U.S. PATENT DOCUMENTS

| 8,754,086 B2 | 6/2014 | Persson et al. |
| 2002/0035111 A1 | 3/2002 | Pamukcu et al. |

FOREIGN PATENT DOCUMENTS

| WO | 98/16526 | 4/1998 |
| WO | 03/017939 A2 | 3/2003 |
| WO | 2010/149943 A1 | 12/2010 |
| WO | 2010/149944 A1 | 12/2010 |

OTHER PUBLICATIONS

Jordan, V.C., "Tamoxifen: A Most Unlikely Pioneering Medicine", Nature Reviews: Drug Discovery, vol. 2, 2003, 205-213.
Hackam, et al., "Translation of Research Evidence from Animals to Humans", JAMA, 296(14), 2006, 1731-1732.
International Search Report, PCT/GB2009/001598, mailed Feb. 8, 2010.
International Search Report, PCT/GB2010/000514, mailed Jan. 4, 2012.

*Primary Examiner* — Douglas M Willis
(74) *Attorney, Agent, or Firm* — K&L Gates LLP; Louis C. Cullman; Brent A. Johnson

(57) ABSTRACT

The disclosure describes compounds of formula I, wherein the wedged bonds, $R^1$, $R^2$, $R^3$, $R^4$, $R^5$, $R^{5a}$, $R^6$, $R^7$, $R^8$, $R^9$, $R^{10}$, $R^{11}$, $R^{12}$, $R^{13}$, $R^{14}$, X and Y have meanings given in the description, and pharmaceutically-acceptable salts thereof; and methods of using such compounds useful in the treatment of cancer and conditions affected by inhibition of angiogenesis. Also provided, are processes for the preparation of formula I, by reacting formula I with other compounds; and processes for the preparation of a pharmaceutical formulation by bringing into association, a compound of formula I, with therapeutic agents and/or a pharmaceutically-acceptable adjuvant, diluent, or carrier.

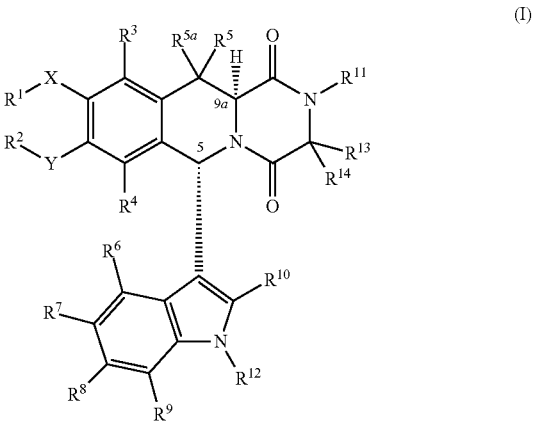

21 Claims, 24 Drawing Sheets

A

B

Control
50 uM 100 uM

Etoposide

50 uM

100 uM

Analogue 1

50 uM

100 uM

Analogue 3

50 uM

100 uM

Analogue 3

INDOLYL-SUBSTITUTED PYRAZINO[1,2-B]ISOQUINOLINES FOR CANCER TREATMENT

CROSS-REFERENCES TO RELATED APPLICATIONS

This application is a continuation of U.S. patent application Ser. No. 13/379,497 filed on Mar. 9, 2012, which is a continuation of PCT application number PCT/GB2010/000514 filed Mar. 19, 2010 which is a continuation of United Kingdom PCT application number GB2009/001598 filed Jun. 25, 2009, the entire disclosures of which are incorporated herein by reference.

FIELD OF THE INVENTION

This invention relates to novel pharmaceutically-useful compounds, which compounds may be useful in the treatment of cancer. The invention also relates to synthetic methods for preparing the compounds.

BACKGROUND OF THE INVENTION

Cancer is a class of diseases that affects people worldwide. Generally, cells in a benign tumor retain their differentiated features and do not divide in a completely uncontrolled manner. A benign tumor is usually localised and non-metastatic.

In a malignant tumor, cells become undifferentiated, do not respond to the body's growth control signals, and multiply in an uncontrolled manner. Malignant tumors are generally divided into two categories: primary and secondary. Primary tumors arise directly from the tissue in which they are found. Secondary tumors may be originated from the primary tumors or may be originated elsewhere in the body, and are capable of spreading to distant sites (metastasizing) or metastasis. The common routes for metastasis are direct growth into adjacent structures, spread through the vascular or lymphatic systems or blood streams.

Tumor metastases are the major cause of mortality in cancer patients. There is compelling evidence that angiogenesis is clinically relevant to the progression and metastasis of cancer. Angiogenesis consists of several steps: the basement membrane degradation, endothelial cell proliferation and migration, and capillary tubule formation. New capillary vessels recruited by tumors deliver nutrients and oxygen into a growing tumor, and remove catabolites and carbon dioxide. Diseases associated with abnormal angiogenesis require or induce vascular growth. For example, corneal angiogenesis involves three phases: a pre-vascular latent period, active neovascularization, and vascular maturation and regression. The identity and mechanism of various angiogenic factors, including elements of the inflammatory response, such as leukocytes, platelets, cytokines, and eicosanoids, or unidentified plasma constituents have yet to be revealed.

This activity is also required for metastasis. One of the important early events in the development of the metastatic phenotype is the induction of genes involved in angiogenesis such as VEGF and other proteins which are released from tumor cells and affect their microenvironment. Cancer cells produce the excess of proangiogenic factors such as vascular endothelial growth factor (VEGF), bFGF (basic fibroblast growth factor), There are seven members of the VEGF family including VEGF-A, VEGF-B, VEGF-C, VEGF-D, VEGF-E, VEGF-F and placental growth factor. VEGF act specifically through tyrosine kinase receptors VEGFR-1, VEGFR-2 and VEGFR-3. The key molecule is VEGF-A (also referred to below as 'VEGF'), induces angiogenesis by promoting proliferation, sprouting, migration and tube formation of endothelial cells. VEGF-A is one of the most potent facilitators of angiogenesis in cancers. VEGF binds to VEGFR-1 and activates the signalling through PI3K-Akt kinases and thus leads to increase in survival and migration. On the other hand, it induces the PLC activity by activation of c-src followed by interaction with VEGFR-2. It has been shown that VEGF expression is associated with metastatic capability in cancer. VEGF may induce disease progression by directly affecting the cell cycle components to accelerate cell proliferation. Metastasis is a very complex process, which occurs through a series of sequential steps including the invasion of adjacent tissue, intravasation, transport through the circulatory system, arrest and growth in a secondary site.

Clinical studies clearly show that tumor cells can undergo a period of dormancy followed by the rapid growth during the relapse. Homing of cancer cells to specific organs remains largely unknown. In carcinomas, the initial step of metastatic dissemination includes the detachment of epithelial cells from the extracellular matrix and disruption of actin cytoskeleton to achieve the round shape. The movement of migrating cells in tissue microenvironments requires proteolytic remodelling of the extracellular matrixes (ECM). The matrix metalloproteinases (MMPs) protein family members play an important role in ECM remodeling and cell invasion. The MMPs are zinc dependent endopeptidases that play multiple roles in biology of ECM, such as release of cryptic fragments and neo-epitopes from ECM macromolecules, release of growth factors and modification of the cell-ECM interface. Most MMPs are secreted proteins: however six of them are membrane proteins. The major function of MMPs is degradation of structural components of the ECM and directly or indirectly migration of cells. Degradation of extracellular matrix not only promotes migration, but also releases the essential growth factors from the matrix storage. Interestingly, MMPs contribute to the vessel remodeling by degradation of type I collagen, regulation of perivascular cells and VEGF processing. The changes of tissue architecture after release of MMPs are due to cleavage of E-cadherins and desmogleins. The expression and interaction of MMPs and TIMPs appear to be involved in invasion and metastases capacity of various cancers.

Several different types of cancer affect the world-wide population, for example those described hereinafter. Prostate cancer (PCa) is one of the most prevalent cancers and a leading cause of cancer related-death worldwide. Incidence of prostate cancer has significantly increased world-wide (Jemal A, Siegel R, Ward E, at al., Cancer statistics, 2006. CA: a cancer journal for clinicians 56: 106-130, 2006; Yin M, Bastacky S, Chandran U, Becich M J and Dhir R: Prevalence of incidental prostate cancer in the general population: a study of healthy organ donors; The Journal of urology 179: 892-895, discussion 895, 2008). Despite recent advances in early diagnosis and treatment, PCa remains the second most lethal cancer in men in the Western World (Jemal et al., ibid, Yin et al., ibid).

Initially, the majority of prostate cancers are responsive to androgen ablation therapy, but most of the tumors eventually will progress to the androgen-refractory state (Gronberg H: Prostate cancer epidemiology. Lancet 361: 859-864, 2003). Once prostate cancer becomes hormone-refractory, cancer cells may rapidly gain the ability to invade and to metastasize to lymph nodes and distant organs (Kalluri R: Basement membranes: structure, assembly and role in tumour angiogenesis. Nature reviews 3: 422-433, 2003).

Tumor metastases are the major cause of mortality in cancer patients. Approximately one-third of treated patients will relapse and no curative treatment currently exists for metastatic disease (Yin et al., ibid; Gronberg H, ibid; Albertsen P C, Hanley J A and Fine J: 20-year outcomes following conservative management of clinically localized prostate cancer. Jama 293: 2095-2101, 2005; Society AC: Cancer Facts & Figures 2008. Atlanta, Ga., American Cancer Society, 2008). The progression from hormone-dependent to hormone-refractory and metastatic prostate cancer is poorly understood. Given the high prevalence of the disease, the aging of the population, and the lack of effective treatment for cancer metastasis, there is an urgent need to discover and develop novel therapeutic approaches.

Primary PCa is treated with hormonal therapy, which is aimed to suppress the androgen production and block androgen receptor (AR)-mediated proliferation and survival pathways. In advanced PCa, androgen deprivation therapy (ADT) is the mainstay treatment. Surgical removal of the tumor and the use of hormone agonists or AR antagonists, such as flutamide, are the major types of ADT (DeMarzo A M, Nelson W G, Isaacs W B and Epstein J I: Pathological and molecular aspects of prostate cancer. Lancet 361: 955-964, 2003).

Docetaxel that targets the mitotic spindle and cell proliferation cycle is being used in advanced PCas. However, as a single agent, Docetaxel has modest activity. Current treatment of advanced metastatic cancer benefits from antiangiogenic drugs. Avastin™, a VEGF inhibitor, targets angiogenic pathways for the treatment of metastatic prostate cancer and has been tested in clinical trials (Di Lorenzo G, Figg W D, Fossa S D, et al: Combination of Bevacizumab and Docetaxel in Docetaxel-Pre-treated Hormone-Refractory Prostate Cancer: A Phase 2 Study. European Urology 54: 1089-1096, 2008). When Avastin™ was used as a single agent or in combination with Docetaxel, the response rate was greatly improved. However, the side effects induced by Docetaxel and Avastin™ may be severe, as the individual drug's toxicities are now combined to cause multiple adverse effects, in particular myelosuppression and heart failure (Friberg L E, Henningsson A, Maas H, Nguyen L and Karlsson M O: Model of chemotherapy-induced myelosuppression with parameter consistency across drugs. J Clin Oncol 20: 4713-4721, 2002). In addition, the costs of these drugs are expensive.

Development of alternative treatments with minimal adverse effect and lower cost will therefore have great clinical and economical benefits.

The effective drug candidate for treatment of metastatic cancer should have the properties to target multiple cancer cell pathways including cell proliferation pathways, apoptosis pathways and angiogenesis signalling. High bioavailability for treatment of aggressive forms of cancer is also important.

The listing or discussion of an apparently prior-published document in this specification should not necessarily be taken as an acknowledgement that the document is part of the state of the art or is common general knowledge.

The compound etoposide is one that has been used in the treatment of various cancers. This compound contains a tetracyclic core, comprising a dioxolyl, tetrahydronaphthyl and tetrahydrofuranyl all fused in a series.

Heterocyclic compounds containing a pyrazinotetrahydro tetrahydroisoquinoline sub-unit, or variants thereof, are known for use as medicament, for example, as described in international patent application WO 98/16526 and journal article Crescendi, Orlando, 1997, *Eur. J. Biochem.*, 247, 66-73. However, none of these documents relate to compounds in which such a sub-unit is substituted with an indolyl group.

Further, the following compound:

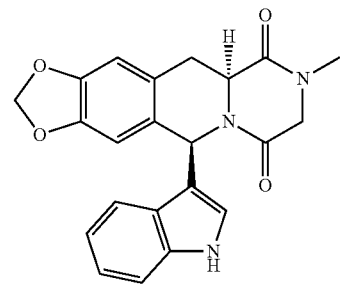 [SMILES: CN1CC(=O)N2[C@@H](c3c[nH]c4ccccc34)c3cc4c(cc3C[C@H]2C1=O)OCO4]

in which the hydrogen at the 9a position is in the S-configuration, and the 3-indolyl group at the 5-position is in the R-configuration (i.e. the above compound is of an absolute stereochemistry), has been isolated from botanical extracts in China. This compound and/or the extracts from which it may be isolated may have shown biological activity as a medicament. However, there is no disclosure regarding the potential synthetic preparation of such compounds, and moreover there is no disclosure of such a compound of a different relative and/or absolute stereochemistry for use as a medicament.

DISCLOSURE OF THE INVENTION

According to the invention, there is now provided a compound of formula I,

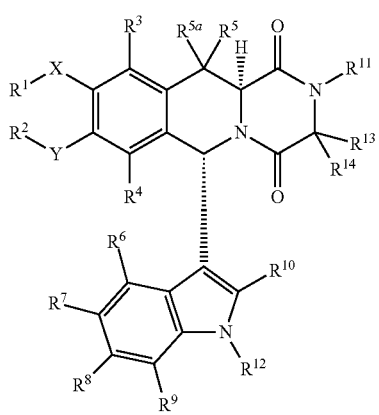

wherein:
the bonds depicted by ┇ represent the relative stereochemistry (i.e. the relevant hydrogen atom and 3-indolyl group are cis with respect to each other);
X and Y independently represent —O—, —N($R^a$)— or either one of these may alternatively represent —N=;
$R^a$ represents H or $C_{1-6}$ alkyl optionally substituted by one or more fluoro atoms;
$R^1$ and $R^2$ independently represent H, $C_{1-6}$ alkyl (optionally substituted by one or more fluoro atoms), —C(O)$C_{1-6}$ alkyl (optionally substituted by one or more fluoro atoms), —CH$_2$-phenyl (which phenyl moiety is optionally substituted by one or more substituents selected from halo and $C_{1-3}$ alkyl), or, $R^1$ and $R^2$ may together represent a $C_{1-2}$ alkylene linker group (i.e. $R^1$ and $R^2$ may be linked together to form, together with the X and Y groups to which they are necessarily attached, a 5- or 6-membered ring in which there is a $C_{1-2}$ alkylene group linking substituents X and Y);

$R^3$ to $R^{19}$ independently represent H, halo, —$OR^b$, —$N(R^c)R^d$, $C_{1-6}$ alkyl (optionally substituted by one or more fluoro atoms) or —$CH_2$-phenyl (which phenyl moiety is optionally substituted by one or more substituents selected from halo and $C_{1-3}$ alkyl); or any two adjacent $R^6$ to $R^9$ groups (i.e. $R^6$ and $R^7$, $R^7$ and $R^8$ or $R^8$ and $R^9$) may be linked together to form a further 3- to 8- (e.g. 5- or 6-) membered ring optionally containing one to three double bonds, optionally containing one to four (e.g. one or two) heteroatoms, and which ring is itself optionally substituted by one or more substituents selected from halo and $C_{1-4}$ alkyl (optionally substituted by one or more fluoro atoms);

$R^b$ represents H, $C_{1-6}$ alkyl (optionally substituted by one or more fluoro atoms) or —$C(O)C_{1-6}$ alkyl (optionally substituted by one or more fluoro atoms);

$R^c$ and $R^d$ independently represent H or $C_{1-6}$ alkyl (optionally substituted by one or more fluoro atoms);

$R^{11}$ and $R^{12}$ independently represent H, $C_{1-6}$ alkyl (optionally substituted by one or more fluoro atoms), —$C(O)C_{1-6}$ alkyl (optionally substituted by one or more fluoro atoms), phenyl (optionally substituted by one or more substituents selected from halo and $C_{1-3}$ alkyl) or —$CH_2$-phenyl (which phenyl moiety is optionally substituted by one or more substituents selected from halo and $C_{1-3}$ alkyl);

$R^{13}$ and $R^{14}$ independently represent H, $C_{1-6}$ alkyl (optionally substituted by one or more fluoro atoms) or —$CH_2$-phenyl (which phenyl moiety is optionally substituted by one or more substituents selected from halo and $C_{1-3}$ alkyl), or a pharmaceutically acceptable salt thereof, which compounds and salts are referred to hereinafter as "the compounds of the invention".

In another embodiment of the invention, there is provided a compound of the invention as hereinbefore described, provided that the compound is not:

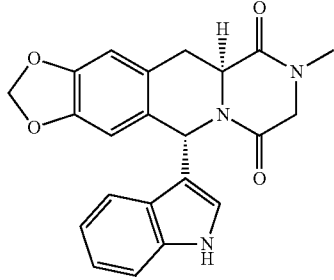 [SMILES: CN1CC(=O)N2[C@H](c3c[nH]c4ccccc34)c3cc4c(cc3C[C@H]2C1=O)OCO4]

i.e. provided that when: X and Y represent —O—; $R^1$ and $R^2$ together represent a —$CH_2$— moiety linking X and Y; $R^3$ to $R^{10}$, $R^{12}$, $R^{13}$ and $R^{14}$ represent hydrogen; $R^{11}$ represents methyl, then when the hydrogen at position 9a is in the S-configuration, the 3-indolyl group is not in the S-configuration, which compounds and salts are also referred to hereinafter as "the compounds of the invention".

For the avoidance of doubt, and given that it is stated hereinbefore that the 3-indolyl group and relevant hydrogen atom (attached by a "wedge" bond) are cis with respect to one another, the following compounds of formula IA and IB are encompassed within the scope of the compounds of the invention:

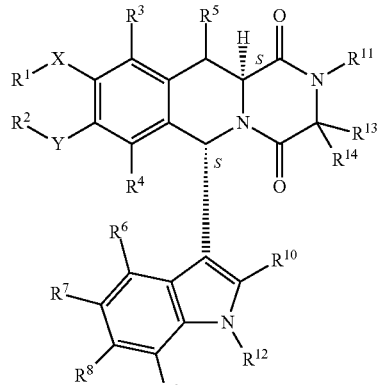

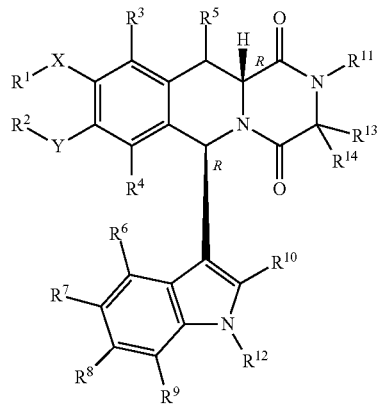

in which the integers are as hereinbefore defined (and $R^{5a}$ is preferably hydrogen; hence its omission), but in which the "wedge" bonds (attached to the 3-indolyl group and to the relevant hydrogen atom) represent bonds of an absolute configuration, as represented by the emboldened "R" or "S". That is, it may be a compound of formula IA in which the 3-indolyl group at the 5-position and the relevant hydrogen atom at the 9a-position are both in the S-configuration, or, a compound of formula IB in which those moieties (the 3-indolyl group at the 5-position and the relevant hydrogen atom at the 9a-position) are both in the R-configuration. Further, the compound of the invention may be a mixture (e.g. a racemic mixture) of those relevant compounds of formula IA and IB (in which the two wedged bonds are either both in the R-configuration or both in the S-configuration), i.e. mixtures of the two different enantiomers of the cis diastereoisomers. Preferably, single enantiomers of compounds of the invention are obtained, for instance in which the enantiomeric excess (ee) is greater than 50:50, e.g. greater than 80:20, such at greater than 90:10 (most preferably in these situations the ee is greater than, or about, 99%; however, this may be contingent on the optical purity of starting materials that may be employed in the synthesis). Most preferably, single enantiomers of compounds of the invention in which the absolute stereochemistry at the two relevant chiral centres is the S-configuration (see compound IA above) are desired.

It is stated herein that the compounds of the invention are those in which the 3-indolyl group in the 5-position and the relevant hydrogen atom in the 9a-position are cis-relatively. By this, we mean that the cis diastereoisomer is present in a ratio of at least 80:20 compared to the un-desired trans diastereoisomer. Preferably, it is present in at least a ratio of 90:10, e.g. at least, or about, 95:5 and most preferably at least, or about, 99:1 (for instance, there is essentially none, or a negligible amount, of the trans diastereoisomer present in the compound of the invention).

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin. For the avoidance of doubt, solvates are also included within the scope of the invention.

Compounds of the invention may contain double bonds and may thus exist as E (entgegen) and Z (zusammen) geometric isomers about each individual double bond. All such isomers and mixtures thereof are included within the scope of the invention.

Compounds of the invention may also exhibit tautomerism. All tautomeric forms and mixtures thereof are included within the scope of the invention.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

Unless otherwise specified, $C_{1-q}$ alkyl groups (where q is the upper limit of the range) defined herein may be straight-chain or, when there is a sufficient number (i.e. a minimum of two or three, as appropriate) of carbon atoms, be branched-chain, and/or cyclic (so forming a $C_{3-q}$-cycloalkyl group). When there is a sufficient number (i.e. a minimum of four) of carbon atoms, such groups may also be part cyclic. Such alkyl groups may also be saturated or, when there is a sufficient number (i.e. a minimum of two) of carbon atoms, be unsaturated (forming, for example, a $C_{2-q}$ alkenyl or a $C_{2-q}$ alkynyl group). Unless otherwise specified, $C_{1-2}$ alkylene groups, as defined herein, refers to —$CH_2$— or —$CH_2$—$CH_2$—, i.e. linear (non-branched alkylene). However, $C_{1-2}$ alkylene also encompasses unsaturated $C_{1-2}$ alkylene, i.e. =C(H)— and —CH=CH—.

The term "halo", when used herein, includes fluoro, chloro, bromo and iodo.

For the avoidance of doubt, when a term such as "$R^1$ to $R^{15}$" is employed herein, this will be understood by the skilled person to mean $R^1$, $R^2$, $R^3$, $R^4$, $R^5$, $R^{5a}$ (although $R^{5a}$ is preferably not present, i.e. it represents hydrogen), $R^6$, $R^7$, $R^8$, $R^9$, $R^{10}$, $R^{11}$, $R^{12}$, $R^{13}$, $R^{14}$ and $R^{15}$ inclusively.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Hence, the compounds of the invention also include deuterated compounds, i.e. in which one or more hydrogen atoms are replaced by the hydrogen isotope deuterium.

All individual features (e.g. preferred features) mentioned herein may be taken in isolation or in combination with any other feature (including preferred features) mentioned herein (hence, preferred features may be taken in conjunction with other preferred features, or independently of them).

The skilled person will appreciate that compounds of the invention that are the subject of this invention include those that are stable. That is, compounds of the invention include those that are sufficiently robust to survive isolation from e.g. a reaction mixture to a useful degree of purity.

Compounds of the invention that may be mentioned include those in which any two adjacent $R^6$ to $R^9$ groups may not be linked together, i.e. $R^8$ to $R^9$ independently represent H, halo, —$OR^b$, —$N(R^c)R^d$, $C_{1-6}$ alkyl (optionally substituted by one or more fluoro atoms) or —$CH_2$-phenyl (which phenyl moiety is optionally substituted by one or more substituents selected from halo and $C_{1-3}$ alkyl).

Other compounds of the invention that may be mentioned include those in which: when any two adjacent $R^6$ to $R^9$ groups (i.e. $R^6$ and $R^7$, $R^7$ and $R^8$ or $R^8$ and $R^9$) are linked together to form a further ring, then that ring is preferably a 5- or 6-membered (e.g. 6-membered) carbocyclic ring, preferably containing double bonds (e.g. one or more, preferably forming a benzene ring, fused to the requisite indolyl group of the compound of formula I);

$R^{5a}$ represents hydrogen.

Preferred compounds of the invention include those in which:

$R^5$ and $R^{5a}$ independently represent hydrogen;

$R^6$ to $R^9$ independently represent: hydrogen; halo; —$OR^b$; —$N(R^c)R^d$; unsubstituted $C_{1-6}$ alkyl; or unsubstituted —$CH_2$-phenyl; or two adjacent $R^6$ to $R^9$ groups (e.g. $R^8$ and $R^9$) are linked together to form a 6-membered ring (e.g. a benzene ring);

any two or three of $R^6$ to $R^9$ (e.g. $R^6$ and $R^8$, and, e.g. optionally, $R^9$) represent hydrogen and the others (e.g. $R^7$) represent hydrogen or a substituent selected from halo (e.g. chloro) and —$OR^b$, or, any two adjacent substituents (e.g. $R^8$ and $R^9$) are linked together to form a further 6-membered ring (e.g. a benzene ring);

$R^{12}$ represents hydrogen, $C_{1-4}$ (e.g. $C_{1-2}$) alkyl (e.g. methyl; which alkyl group is preferably unsubstituted) or —$CH_2$-phenyl.

Preferred compounds of the invention that may be mentioned include those in which:

$R^a$ represents H or unsubstituted $C_{1-6}$ alkyl;

$R^1$ and $R^2$ independently represent: H; unsubstituted $C_{1-6}$ alkyl; unsubstituted —C(O)$C_{1-6}$ alkyl; unsubstituted —$CH_2$-phenyl; or, $R^1$ and $R^2$ may together represent a $C_{1-2}$ alkylene linker group;

$R^3$ to $R^{10}$ independently represent: —$N(R^c)R^d$; or preferably H; halo; —$OR^b$; unsubstituted alkyl; or unsubstituted —$CH_2$-phenyl (more preferably, at least five (e.g. at least six) of $R^3$ to $R^{19}$ represent hydrogen, i.e. only two or preferably one of $R^3$ to $R^{19}$ represents a substituent other than hydrogen);
$R^b$ represents unsubstituted —C(O)C$_{1-6}$ alkyl or, preferably, H or unsubstituted C$_{1-6}$ alkyl;
$R^c$ and $R^d$ independently represent H or unsubstituted C$_{1-6}$ alkyl;
$R^{11}$ and $R^{12}$ independently represent: unsubstituted —C(O)C$_{1-6}$ alkyl, unsubstituted —CH$_2$-phenyl; or, preferably, H; unsubstituted C$_{1-6}$ alkyl; or unsubstituted phenyl;
$R^{13}$ and $R^{14}$ independently represent unsubstituted —CH$_2$-phenyl or, preferably H or unsubstituted C$_{1-6}$ alkyl;
preferred substituents on phenyl moieties include halo (e.g. fluoro and chloro) and methyl.

More preferred compounds of the invention that may be mentioned include those in which:
$R^a$ represents hydrogen;
$R^1$ and $R^2$ independently represent hydrogen or C$_{1-3}$ alkyl (e.g. methyl) or $R^1$ and $R^2$ together represent —CH$_2$—, —CH$_2$CH$_2$— or —C(H)=(linking together X and Y);
both of X and Y represents —O—; either one of X and Y represents —O— and the other represents —N($R^a$)— or —N= (in this instance, $R^1$ and $R^2$ preferably represent —CH$_2$— or —C(H)=); or either one of X and Y represents —N($R^a$)— and the other represents —O— or —N= (in this instance, $R^1$ and $R^2$ preferably represent —CH$_2$— or —C(H)=);
$R^3$ to $R^{10}$ independently represent hydrogen or —OR$^b$ (for instance, any one of $R^3$ to $R^{15}$, e.g. $R^5$, may represent —OR$^b$ or hydrogen and the others represent hydrogen);
$R^b$ represents hydrogen;
$R^{13}$ and $R^{14}$ independently represent hydrogen;
$R^{11}$ represents C$_{1-4}$ (e.g. C$_{1-3}$) alkyl (e.g. methyl, ethyl or n-propyl) or unsubstituted phenyl;
$R^{12}$ represents hydrogen or C$_{1-3}$ alkyl (e.g. methyl);
the requisite 3-indolyl moiety in the 5-position is in the S-configuration;
the hydrogen atom at the 9a-position is in the S-configuration.

Preferred rings that X, Y, $R^1$ and $R^2$ (when the latter two represent a C$_{1-2}$ alkylene group linking X and Y) may represent include:

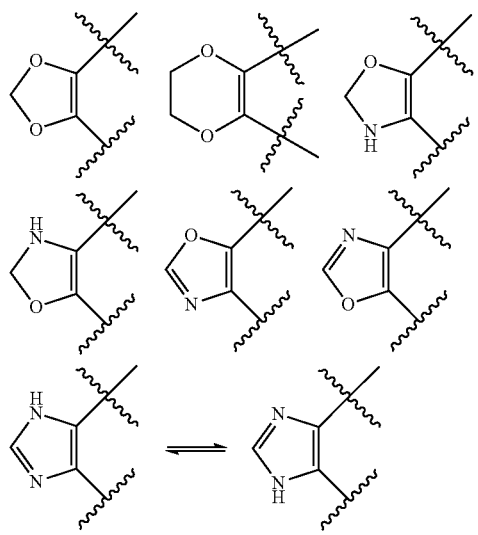

for instance a 1,3-dioxolyl group, a 1,4-dioxinyl group (preferably a 2,3-dihydro-[1,4]-dioxinyl group), an oxazolyl group (e.g. oxazolyl or 2,3-dihydro-oxazolyl) or an imidazolyl group (the skilled person will appreciate that the two imidazolyl groups depicted may exist in equilibrium, due to tautomerism). When $R^1$ and $R^2$ are not linked together, then such groups independently represent hydrogen or C$_{1-3}$ alkyl (e.g. methyl), for instance, —X—$R^1$ and —Y—$R^2$ independently represent —OH or —OCH$_3$ (for instance, —X—$R^1$ and —Y—$R^2$ both represent —OH or both represent —OCH$_3$).

Further preferred compounds of the invention that may be mentioned include those in which:

X and Y independently represent —O—;

$R^1$ and $R^2$ together represent a —CH$_2$— linker group, linking X and Y to form a 1,3-dioxolyl moiety, i.e.:

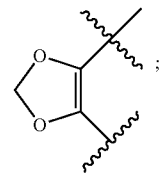 [SMILES: *C1=C(*)OCO1]

$R^3$, $R^4$, $R^5$, $R^6$, $R^7$, $R^8$, $R^9$, $R^{10}$, $R^{12}$, $R^{13}$ and $R^{14}$ independently represent hydrogen;

$R^{11}$ represents C$_{1-3}$ alkyl (e.g. methyl);

the requisite 3-indolyl moiety is in the S-configuration;

the hydrogen atom at the 9a-position is in the S-configuration.

Compounds of the invention may be made in accordance with techniques that are well known to those skilled in the art, for example as described hereinafter.

According to a further aspect of the invention there is provided a process for the preparation of a compound of formula I which process comprises:

(I) for compounds of formula I in which $R^1$ and $R^2$ are linked together, reaction of a compound of formula I in which $R^1$ and $R^2$ both represent hydrogen (or a protected derivative thereof), with a compound of formula II, $$L^1\text{-}R^{1/2}\text{-}L^2 \qquad \text{II}$$

wherein $L^1$ and $L^2$ independently represent suitable leaving groups, such as a sulfonate group (e.g. —OS(O)$_2$CF$_3$, —OS(O)$_2$CH$_3$, —OS(O)$_2$PhMe or a nonaflate), chloro, bromo, or, preferably, iodo, and $R^{1/2}$ represents C$_{1-2}$ alkylene (as hereinbefore defined in respect of the linkage of $R^1$ and $R^2$), under standard reaction conditions, for example in the presence of a suitable base, such as NaH, NaOH, Na$_2$CO$_3$, K$_2$CO$_3$, K$_3$PO$_4$, Cs$_2$CO$_3$, an alkoxide base (such as t-BuONa or t-BuOK, or the like) or an amine base (such as Et$_3$N, pyridine, tributylamine, trimethylamine, dimethylaminopyridine, diisopropylamine and diisopropylethylamine, or the like), or mixtures of bases, and an appropriate solvent such as toluene, dichloromethane, acetonitrile or a polar aprotic solvent (such as tetrahydrofuran, dioxane, diethyl ether, dimethylsulfoxide or dimethylformamide), or mixtures thereof. Preferred base includes Cs$_2$CO$_3$ and preferred solvents include dimethylformamide. Such a reaction may take place at room temperature, but is preferably at elevated temperature (e.g. above 100° C., such as at about 150° C.);

(ii) compounds of formula I, or protected derivatives thereof, may also be prepared by reaction of a compound of formula III,

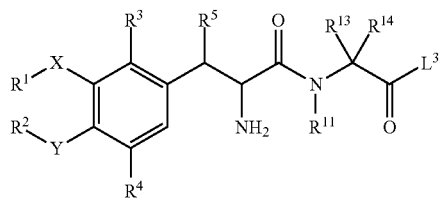

III (or a single enantiomer thereof; e.g. a chiral amine in which the bond bearing the —NH$_2$ group is of a certain configuration) wherein L$^3$ represents a suitable leaving such as one hereinbefore defined in respect of L$^1$ and L$^2$ (e.g. iodo, bromo or chloro), but preferably represents —OR$^a$ (in which R$^a$ preferably represents C$_{1-6}$ alkyl, e.g. methyl), and R$^1$, R$^2$, R$^3$, R$^4$, R$^5$, R$^{11}$, R$^{13}$, R$^{14}$, X and Y are as hereinbefore defined, with a compound of formula IV,

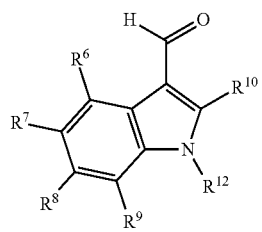

IV or a protected derivative thereof, wherein R$^6$, R$^7$, R$^8$, R$^9$, R$^{10}$ and R$^{12}$ are as hereinbefore defined, under condensation and cyclisation reaction conditions, for example in the presence of acetic acid and sodium acetate (although different solvents and/or bases may be employed), which reaction may produce an intermediate of formula V as defined hereinafter. Thereafter (for example, if an acid addition salt, e.g. a AcOH salt, of the intermediate compound of formula V is formed), the reaction mixture may be neutralised (e.g. by the addition of NaHCO$_3$ (aq. sat.)), which may result in the formation of the compound of formula I, for example by an intramolecular cyclisation reaction of any intermediate compound of formula V that may be formed. The skilled person will appreciate that the stereochemistry of the compound of formula III may influence the stereochemistry of the compound of formula I so formed. For example, if the compound of formula III contains a chiral centre of a certain configuration, then the stereospecificity of the starting material may govern the stereochemistry of the product (e.g. of formula I) so formed. For example, a compound of formula III with the absolute stereochemistry as depicted by formula IIIA in the following scheme may produce a compound of formula I with the absolute stereochemistry depicted by formula IA, in the following scheme:

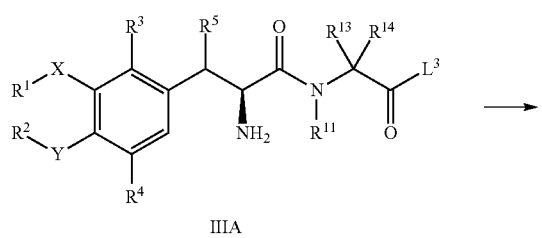

IIIA

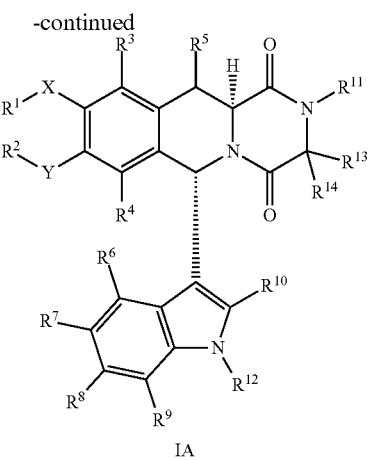

IA

Equally, the skilled person will appreciate that, starting from a racemic form of a compound of formula III will enable the preparation of any of the diastereoisomers and/or enantiomers of the compound of formula I (e.g. by separation of diastereoisomers, e.g. by chromatography such as HPLC, and by separation of enantiomers, e.g. by resolution);

(iii) intramolecular cyclisation of a compound of formula V,

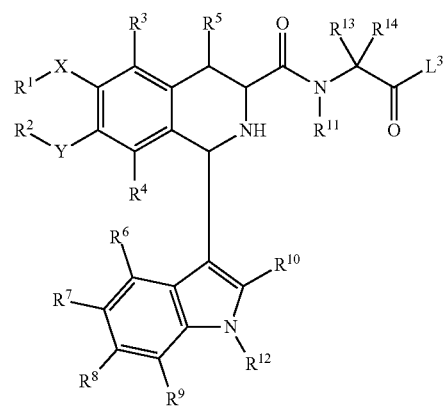

V or a salt thereof (e.g. an acid addition salt, such as an AcOH salt), or a single enantiomer thereof (single enantiomer and single cis-diastereoisomer), wherein R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, X and Y are as hereinbefore defined, which may be performed under standard conditions, for example when an acid addition salt of the compound of formula V is employed (e.g. if it is formed in situ), then neutralisation may be effected (e.g. under conditions such as those described in respect of step (ii) above) first. The intramolecular cyclisation (i.e. nucleophilic substitution at the carbonyl group) may occur naturally or may be promoted by the addition of a suitable base; or (iv) compounds of formula I in which R$^{11}$ and/or R$^{12}$ represent a substituent other than hydrogen (e.g. in which both represent a substituent other than hydrogen) may be prepared from a corresponding compound of formula I in which R$^{11}$ and/or R$^{12}$ represents hydrogen, with a compound of (or two different compounds of) formula VA, $$R^{11/12}-L^4 \qquad \text{VA}$$

wherein R$^{11/12}$ represents R$^{11}$ or R$^{12}$ (depending on the position to which attachment is desired) provided that it does not represent hydrogen, in the presence of base (such as one described in respect of process step (i) above; e.g. NaH) and an appropriate solvent (such as one described in process step (i) above; e.g. a polar aprotic solvent such as dimethylformamide) under standard conditions known to those skilled in the art. The skilled person will appreciate that these reactions conditions will work for the preparation of compounds in which $R^{11/12}$ represents $C_{1-6}$ alkyl, —C(O)—$C_{1-6}$ alkyl or —CH$_2$phenyl (in which the alkyl and phenyl moieties are optionally substituted as hereinbefore defined). For the preparation of compounds in which $R^{11/12}$ represents optionally substituted phenyl, different conditions may need to be employed, for instance, coupling reaction conditions in the presence of an appropriate catalyst (e.g. Pd(OAc)$_2$ or the like), an optional additive, base and suitable solvent.

Compounds of formula III may be prepared by reaction of a compound of formula VI,

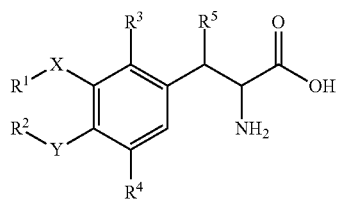

VI or a protected derivative thereof (e.g. an amino-protected derivative, e.g. —NHBoc protected derivative, or an ester thereof), or, a single enantiomer thereof, wherein $R^1$, $R^2$, $R^3$, $R^4$, $R^5$, X and Y are as hereinbefore defined, with a compound of formula VII,

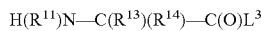

VII wherein $R^{11}$, $R^{13}$, $R^{14}$ and $L^3$ are as hereinbefore defined (and $L^3$ is preferably —OR$^a$ as defined above), under standard amide coupling reaction conditions, for example in the presence of a suitable coupling reagent (e.g. 1,1'-carbonyldiimidazole, N,N'-dicyclohexylcarbodiimide, 1-(3-dimethylaminopropyl)-3-ethylcarbodiimide (or hydrochloride thereof), N,N'-disuccinimidyl carbonate or most preferably bis(2-oxo-3-oxazolidinyl)phosphonic chloride (i.e. Bop-Cl), or the like), optionally in the presence of a suitable base (e.g. sodium hydride, sodium bicarbonate, potassium carbonate, pyridine, triethylamine, dimethylaminopyridine, diisopropylamine, sodium hydroxide, potassium tert-butoxide and/or lithium diisopropylamide (or variants thereof) and an appropriate solvent (e.g. tetrahydrofuran, pyridine, toluene, dichloromethane, chloroform, acetonitrile, dimethylformamide, trifluoromethylbenzene, dioxane or triethylamine). Preferred coupling agents include Bop-Cl, preferred bases include triethylamine and/or sodium bicarbonate (e.g. a mixture thereof) and the preferred solvent system is dichloromethane (in this instance, the reaction mixture may be allowed to react at room temperature or thereabouts for a period of time). Alternatively, the carboxylic acid group of the compound of formula VI may be converted under standard conditions to the corresponding acyl chloride (e.g. in the presence of SOCl$_2$ or oxalyl chloride), which acyl chloride is then reacted with a compound of formula VII, for example under similar conditions to those mentioned above.

Compounds mentioned herein (e.g. those of formulae II, IV, VA, VI and VII, as well as certain other compounds of formula III) are either commercially available, are known in the literature, or may be obtained either by analogy with the processes described herein, or by conventional synthetic procedures, in accordance with standard techniques, from available starting materials using appropriate reagents and reaction conditions. In this respect, the skilled person may refer to inter alia "Comprehensive Organic Synthesis" by B. M. Trost and I. Fleming, Pergamon Press, 1991.

The substituents $R^2$, $R^3$, $R^4$, $R^5$, $R^6$, $R^7$, $R^8$, $R^9$, $R^{10}$, $R^{11}$, $R^{12}$, $R^{13}$, $R^{14}$, X and Y in final compounds of the invention or relevant intermediates may be modified one or more times, after or during the processes described above by way of methods that are well known to those skilled in the art. Examples of such methods include substitutions, reductions, oxidations, alkylations, acylations, hydrolyses, esterifications, etherifications, halogenations or nitrations. Such reactions may result in the formation of a symmetric or asymmetric final compound of the invention or intermediate. The precursor groups can be changed to a different such group, or to the groups defined in formula I, at any time during the reaction sequence. In this respect, the skilled person may also refer to "Comprehensive Organic Functional Group Transformations" by A. R. Katritzky, O. Meth-Cohn and C. W. Rees, Pergamon Press, 1995.

Compounds of the invention may be isolated from their reaction mixtures using conventional techniques (e.g. recrystallisations).

It will be appreciated by those skilled in the art that, in the processes described above and hereinafter, the functional groups of intermediate compounds may need to be protected by protecting groups.

For instance, amino groups may be protected with a Boc group, by reaction in the presence of base (e.g. NaOH or an amine base, such as triethylamine, dimethylaminopyridine, or the like) with Boc$_2$O and a suitable solvent (e.g. water or a polar aprotic solvent such as dioxane, tetrahydrofuran, diethyl ether, or mixtures thereof). Standard deprotection reaction conditions include deprotection in the presence of acid (e.g. in the presence of HCl in a solvent, such as a polar aprotic solvent).

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques. By 'protecting group' we also include suitable alternative groups that are precursors to the actual group that it is desired to protect. For example, instead of a 'standard' amino protecting group, a nitro or azido group may be employed to effectively serve as an amino protecting group, which groups may be later converted (having served the purpose of acting as a protecting group) to the amino group, for example under standard reduction conditions described herein. Protecting groups that may be mentioned include lactone protecting groups (or derivatives thereof), which may serve to protect both a hydroxy group and an α-carboxy group (i.e. such that the cyclic moiety is formed between the two functional groups.

The type of chemistry involved will dictate the need, and type, of protecting groups as well as the sequence for accomplishing the synthesis.

The use of protecting groups is fully described in "Protective Groups in Organic Synthesis", 3$^{rd}$ edition, T. W. Greene & P. G. M. Wutz, Wiley-Interscience (1999).

In yet a further embodiment of the invention, there is provided a synthetic form of a compound of the invention (i.e. a compound of formula I (or salt thereof)), which is characterised by virtue of the fact that it is made synthetically for example in accordance with the processes described herein. Such compounds are also referred to herein as "compounds of the invention".

Medical and Pharmaceutical Uses

Compounds of the invention are indicated as pharmaceuticals. According to a further aspect of the invention there is provided a compound of the invention, as hereinbefore (but without any provisos, where applicable), for use as a pharmaceutical. There is also provided a synthetic form of a compound of the invention (but without any provisos, where applicable), for use as a pharmaceutical.

For the avoidance of doubt, although compounds of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the "active" compounds to which they are metabolised) may therefore be described as "prodrugs" of compounds of the invention.

By "prodrug of a compound of the invention", we include compounds that form a compound of the invention, in an experimentally-detectable amount, within a predetermined time (e.g. about 1 hour), following oral or parenteral administration. All prodrugs of the compounds of the invention are included within the scope of the invention.

Furthermore, certain compounds of the invention may possess no or minimal pharmacological activity as such, but may be administered parenterally or orally, and thereafter be metabolised in the body to form compounds of the invention that possess pharmacological activity as such. Such compounds (which also includes compounds that may possess some pharmacological activity, but that activity is appreciably lower than that of the "active" compounds of the invention to which they are metabolised), may also be described as "prodrugs".

Thus, the compounds of the invention are useful because they possess pharmacological activity, and/or are metabolised in the body following oral or parenteral administration to form compounds which possess pharmacological activity.

Compounds of the invention (as hereinbefore defined but without the proviso(s)) may be useful in the treatment of a cancer. By "cancer", we mean any disease that arises from an uncontrolled growth of cells (e.g. uncontrolled division), invasion (e.g. direct growth into adjacent tissue) or metastasis. By "uncontrolled growth", we include an increase in the number and/or size of cancer cells (also referred to herein as "proliferation"). By "metastasis" we mean the movement or migration (e.g. invasiveness) of cancer cells from a primary tumor site in the body of a subject to one or more other areas within the subject's body (where the cells can then form secondary tumors). Thus, in one embodiment the invention provides compounds and methods for inhibiting, in whole or in part, the formation of secondary tumors in a subject with cancer.

Advantageously, the compounds of the invention may be capable of inhibiting the proliferation and/or metastasis of cancer cells selectively.

By "selectively" we mean that the compounds of the invention may inhibit the proliferation and/or metastasis of cancer cells to a greater extent than it modulates the function (e.g. proliferation) of non-cancer cells. Preferably, the compounds of the invention inhibit the proliferation and/or metastasis of cancer cells only.

Compounds of the invention may be suitable for use in the treatment of any cancer type, including all tumors (non-solid and solid tumors). The cancer type may include (but is not limited to) benign tumors (such as hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas) and malignant tumors (such as leukemia, myelodysplastic syndromes (MDS), prostate cancer, breast cancer, skin cancer, bone cancer, liver cancer, lung cancer, brain cancer, cancer of the larynx, bladder, gall bladder, ovary, cervix, pancreas, rectum, parathyroid, thyroid, esophagus, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, non-small cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas). Others that may be mentioned include cancers of the testis, genitourinary tract, glioblastoma, neuroblastoma, keratoacanthoma, epidermoid carcinoma, large cell carcinoma, follicular carcinoma, undifferentiated carcinoma, papillary carcinoma, seminona, myeloid disorders, lymphoid disorders, hairy cells, buccal cavity and pharynx (oral), lip, tongue, mouth, small intestine, colon-rectum, large intestine, rectum, brain and central nervous system, Hodgkin's and leukaemia; hematopoietic tumors of lymphoid lineage, including leukemia, acute iymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xeroderma pigmentosum, keratoxanthoma, thyroid follicular cancer and Kaposi's sarcoma.

In particular, compounds of the invention may possess potent inhibitory activity on the growth and invasion of hormone-refactory and aggressive human prostate tumors (for example, as may be shown in xenograft mouse models). It is particularly preferred therefore that the compounds of the invention may be useful in the treatment of aggressive cancers such as prostate cancer.

Compounds of the invention may reduce the rate of cell proliferation when tested in an assay using a PC-3 cancer cell line (e.g. obtained from ATCC). The compounds may thus possess a beneficial inhibitory effect on the ability of tumors of this type, and of cancers generally, to survive. The PC-3 cancer cell line has several properties that represent the hormone-independent and invasive prostate cancer. For instance, PC-3 cells lack functional androgen receptor (AR) signalling, grow rapidly in culture medium and can form large and very aggressive tumors when implanted into nude mice. Hence, the biological tests described hereinafter (e.g. PC-3 xenograft mouse models) provide a sound predication of the utility of the compounds tested by mimicking the gradual dissemination of prostate carcinoma cells in viva Further, it has been reported that even the widely used cancer drugs such as Avastin™ or Docetaxel alone or in combination had low inhibitory effect on PC-3 cells (Petrylak DP: Future directions in the treatment of androgen-independent prostate cancer. Urology 65: 8-12, 200538.2007; and Hung H: Bevacizumab plus 5-fluorouracil induce growth suppression in the CWR-22 and CWR-22R prostate cancer xenografts. Molecular cancer therapeutics 6: 2149-2157, 2007).

The compounds of the invention may target multiple cellular pathways that are associated with tumor growth, angiogenesis and metastasis. The compounds of the invention may also affect other cancer pathways, such as cell cycle regulation and apoptosis.

The compounds of the invention may therefore be VEGF (vascular endothelial growth factor) inhibitors, e.g. they may inhibit the expression of VEGF receptors including but not limited to VEGF and/or VEGF receptor 2 (as may be shown in a test described herein). This may occur selectively, or, may be one of a plurality of the mechanisms by which the compounds of the invention act to treat cancer. The VEGF signalling pathway is known to be linked to tumor vascularisation and invasion, and hence compounds of the invention may possess anti-cancer effects by inhibiting angiogenesis (and may therefore be classed as anti-angiogenesis agents). In another embodiment of the invention therefore, the compounds of the invention may be useful in the treatment of a disease in which the inhibition of angiogenesis (and/or VEGF) is desired and/or required.

The term "inhibition" may refer to any measurable reduction and/or prevention, which in the context of angiogenesis refers to the reduction and/or prevention of angiogenesis (e.g. the expression of VEGF receptors including but not limited to VEGF and VEGF receptor 2). The inhibitory activity may be measured by comparing the angiogenesis inhibition in a sample containing a compound of the invention and (a) VEGF receptor(a), such as VEGF and/or VEGF receptor 2, with an equivalent sample of in the absence of a compound of the invention. The measurable change may be objective (e.g. measurable by some test or marker, for example in an in vitro or in vivo assay or test, such as one described hereinafter, or otherwise another suitable assay or test known to those skilled in the art) or subjective (e.g. the subject gives an indication of or feels an effect).

Compounds of the invention are indicated both in the therapeutic and/or prophylactic treatment of the above-mentioned conditions.

According to a further aspect of the present invention, there is provided a method of treatment of a disease (e.g. cancer or another disease as mentioned herein) which may be associated with, or affected by, angiogenesis (and/or VEGF; e.g. an inhibition of the expression of VEGF and/or VEGF receptor 2) is desired and/or required, which method comprises administration of a therapeutically effective amount of a compound of the invention but without the proviso(s), as hereinbefore defined, to a patient suffering from, or susceptible to, such a condition.

"Patients" include mammalian (including human) patients. Hence, the method of treatment discussed above may include the treatment of a human or animal body.

The term "effective amount" refers to an amount of a compound, which confers a therapeutic effect on the treated patient. The effect may be objective (e.g. measurable by some test or marker) or subjective (e.g. the subject gives an indication of or feels an effect).

Compounds of the invention may be administered orally, intravenously, subcutaneously, buccally, rectally, dermally, nasally, tracheally, bronchially, sublingually, by any other parenteral route or via inhalation, in a pharmaceutically acceptable dosage form.

Compounds of the invention may be administered alone, but are preferably administered by way of known pharmaceutical formulations, including tablets, capsules or elixirs for oral administration, suppositories for rectal administration, sterile solutions or suspensions for parenteral or intramuscular administration, and the like. The type of pharmaceutical formulation may be selected with due regard to the intended route of administration and standard pharmaceutical practice. Such pharmaceutically acceptable carriers may be chemically inert to the active compounds and may have no detrimental side effects or toxicity under the conditions of use.

Such formulations may be prepared in accordance with standard and/or accepted pharmaceutical practice. Otherwise, the preparation of suitable formulations may be achieved non-inventively by the skilled person using routine techniques and/or in accordance with standard and/or accepted pharmaceutical practice.

According to a further aspect of the invention there is thus provided a pharmaceutical formulation including a compound of the invention, as hereinbefore defined but without the proviso(s), in admixture with a pharmaceutically acceptable adjuvant, diluent and/or carrier.

Depending on e.g. potency and physical characteristics of the compound of the invention (i.e. active ingredient), pharmaceutical formulations that may be mentioned include those in which the active ingredient is present in at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The amount of compound of the invention in the formulation will depend on the severity of the condition, and on the patient, to be treated, as well as the compound(s) which is/are employed, but may be determined non-inventively by the skilled person.

The invention further provides a process for the preparation of a pharmaceutical formulation, as hereinbefore defined, which process comprises bringing into association a compound of the invention, as hereinbefore defined, or a pharmaceutically acceptable ester, amide, solvate or salt thereof with a pharmaceutically-acceptable adjuvant, diluent or carrier.

Compounds of the invention may also be combined with other therapeutic agents that may be useful in the treatment of a cancer and/or a proliferative disease (e.g. another VEGF inhibitor as described herein). Compounds of the invention may also be combined with other therapies.

According to a further aspect of the invention, there is provided a combination product comprising:

(A) a compound of the invention, as hereinbefore defined but without the proviso(s); and
(B) one or more therapeutic agent(s) that is useful in the treatment of cancer and/or a proliferative disease,
wherein each of components (A) and (B) is formulated in admixture with a pharmaceutically-acceptable adjuvant, diluent or carrier.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:
(1) a pharmaceutical formulation including a compound of the invention, as hereinbefore defined but without the proviso(s), one or more therapeutic agent(s) that is useful in the treatment of cancer and/or a proliferative disease, and a pharmaceutically-acceptable adjuvant, diluent or carrier; and
(2) a kit of parts comprising components:
(a) a pharmaceutical formulation including a compound of the invention, as hereinbefore defined but without the proviso(s), in admixture with a pharmaceutically-acceptable adjuvant, diluent or carrier; and
(b) a pharmaceutical formulation including one or more therapeutic agent(s) that is useful in the treatment of cancer and/or a proliferative disease in admixture with a pharmaceutically-acceptable adjuvant, diluent or carrier,
which components (a) and (b) are each provided in a form that is suitable for administration in conjunction with the other.

The invention further provides a process for the preparation of a combination product as hereinbefore defined but without the proviso(s), which process comprises bringing into association a compound of the invention, as hereinbefore defined, or a pharmaceutically acceptable ester, amide, solvate or salt thereof with the other therapeutic agent (or agents) that is (or are) useful in the treatment of cancer and/or a proliferative disease, and at least one pharmaceutically-acceptable adjuvant, diluent or carrier.

By "bringing into association", we mean that the two components are rendered suitable for administration in conjunction with each other.

Thus, in relation to the process for the preparation of a kit of parts as hereinbefore defined, by bringing the two components "into association with" each other, we include that the two components of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Depending on the disorder, and the patient, to be treated, as well as the route of administration, compounds of the invention may be administered at varying therapeutically effective doses to a patient in need thereof. However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Administration may be continuous or intermittent (e.g. by bolus injection). The dosage may also be determined by the timing and frequency of administration. In the case of oral or parenteral administration the dosage can vary from about 0.01 mg to about 10 g (e.g. 1000 mg) per day of a compound of the invention. For example, the dose range may be between 1 mg/kg and 1000 mg/kg (e.g. between 10 mg/kg and 500 mg/kg, preferably between about 20 mg/kg and 200 mg/kg) such as the does ranges employed in the mouse models described hereinafter.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

Compounds of the invention may have the advantage that they target multiple pathways involving tumor growth, apoptosis, angiogenesis and metastases. The compounds of the invention may also be effective angiogenesis inhibitors (and/or VEGF inhibitors), i.e. they may (for example, selectively, or as one mode of action) inhibit angiogenesis (and/or VEGF; e.g. they may inhibit the expression of VEGF and VEGF receptor 2).

Compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise.

For instance, compounds of the invention may be well tolerated by the patient, i.e. show less or no side effects (e.g. weight loss or other toxic side effects) for example as compared to other therapeutic agents. This may be the case even at high concentrations/doses of the compounds of the invention. The compounds of the invention may also display good potency (e.g. better potency than other therapeutic agents) at a relatively or comparatively lower dose. Hence the compound of the invention may have a large therapeutic window.

The compounds of the invention may have advantages over other known chemotherapeutic agents (e.g. Avastin™, Docetaxel and/or Etoposide), which includes better potency and better safety profile (i.e. reduced side effects). Such comparative advantages may be shown in biological tests such as those described hereinafter.

Preferred, non-limiting examples which embody certain aspects of the invention will now be described, with reference to the following figures:

FIG. 1: Tolerance of Healthy Mice to compound of Example 1 (also referred to herein as "Substance X") Treatment at Various Doses A. Healthy mice were treated with 100 mg/kg of Substance X once every other day for 13 days. Body weight of each mouse was measured periodically from Day 1 to Day 13 and the values are mean±standard deviation (SD).

B. Healthy mice were treated with 200 mg/kg of Substance X once every other day for 13 days. Body weight of each mouse was measured once every other day and the values are mean±standard deviation (SD).

FIG. 2: Inhibition of Tumor Growth in Xenograft Animal Model with Large Sized Tumors When the tumors in PC-3 implanted mice grew to 500-600 mm$^3$ in size, the mice were treated with 40 mg/kg of Substance X or solvent (Control) intravenously for 20 days and the tumor size was measured periodically. The tumor size values are mean±standard deviation (SD).

FIG. 3: Inhibition of Tumor Growth in Xenograft Animal Model by Oral Administration of Substance X When the tumors in PC-3 implanted mice grew to 300-350 mm$^3$ in size, the mice were treated with 40 mg/kg of Substance X or solvent (Control). Substance X was orally administrated.

FIG. 4: Inhibition of Tumor Growth in Xenograft Animal Model by Etoposide and Substance X When the tumors in PC-3 implanted mice grew to 200-300 mm$^3$ in size, the mice were treated with 20 mg/kg of Etoposide, 40 mg/kg of Substance X or solvent (Control) by IV once every other day for 14 days. The tumor size was measured periodically and the tumor size values are mean±standard deviation (SD).

FIG. 5: Effect of Substance X on Expression of VEGF and VEGF Receptor 2 Immunohistochemical analysis of VEGF and VEGF receptor 2 was performed in tumors from the Control mice and the mice treated with Substance X. The representative pictures are shown. Tumor sections (Control) or (Substance X) were stained with antibody against human VEGF and VEGF Receptor 2.

FIG. 6: Histology Section of Whole Tumors from Control and Substance X Treated Mice and Evaluation of the effect of Substance X on Vascularisation A. Comparison of the appearance and histology of one pair of tumors stained with anti-VEGF receptor 2 antibody.

B. Immunohistochemical analysis of tumors from the Control mice and mice treated with Substance X for the expression of CD31. Tumor sections (Control) or (Substance X) were stained with antibody against CD31. (B). Regions of high vascular density at centre or the edge areas within the tumors were examined. The number of CD31-positive pixels per microscopic field was recorded. At least two sections per tumor and three views per section were determined. The statistical T-test was performed and was two-sided and P value less than 0.05 was considered to be statistically significant, P value less than 0.01 is labelled as two asterisks.

FIG. 7: Effect of Lund University and Enamine synthesized Compound X on PC-3 cells growth. The number of viable cells after 48 hours. A, Values are the mean±standard deviation. B, Dose response curve for growth inhibitory effect.

FIG. 8: Effect of Example 2 (Analogue 1) on PC-3 cells growth. The number of viable cells after 48 hours. A, Values are the mean±standard deviation. B, Dose response curve for growth inhibitory effect.

FIG. 9: Effect of Example 3 (Analogue 2) on PC-3 cells growth. The number of viable cells after 48 hours. A, Values are the mean±standard deviation. B, Dose response curve for growth inhibitory effect.

FIG. 10: Effect of Example 4 (Analogue 3) on PC-3 cells growth. The number of viable cells after 48 hours. A, Values are the mean±standard deviation. B, Dose-response curve for growth inhibitory effect.

FIG. 11: Effect of Example 5 (Analogue 4) on PC-3 cells growth. The number of viable cells after 48 hours. A, Values are the mean±standard deviation. B, Dose-response curve for growth inhibitory effect.

FIG. 12: Effect of Example 6 (Analogue 5) on PC-3 cell growth. The number of viable cells after 48 hours. A, Values are the mean±standard deviation. B, Dose response curve for growth inhibitory effect.

FIG. 13: Side by side comparison the effect of Analogues 1 and 3 with Etoposide and Docetaxel. The number of viable cells after 48 hours. Values are the mean±standard deviation.

FIG. 14: The antitumor effect of Anaolgue 1 and 3 on U937 human leukemic monocyte lymphoma cell line.

FIG. 15: Time-point cell proliferation analysis after treatment at 1050 analogues' concentrations: Compound X 30 uM, Analogue 1 36 uM, Analogue 2 60 uM, Analogue 3 32 uM, Analogue 4 30 uM.

FIG. 16: Results of various compounds tested in the BrdU assay.

FIGS. 17, 18, 19 and 20: Results of certain examples in the apoptosis assay

FIGS. 21, 22, 23 and 24: Results of certain examples in the cell cycle analysis

EXAMPLES/BIOLOGICAL TESTS

Materials were obtained from commercial suppliers and were used without further purification unless otherwise noted. All moisture and air-sensitive reactions were carried out under an atmosphere of dry nitrogen using oven-dried glassware. High-resolution mass spectra (ESI) were recorded on a Micromass Q-TOF micro spectrometer. NMR spectra were recorded on a Bruker Avance II at 400 MHz ($^1$H) and chemical shifts are relative to the residual peak of the deuterated solvent. All flash chromatography was performed on 60 Å 35-70 μm Matrex silica gel. TLC analyses were made on silica Gel 60 $F_{254}$ (Merck) plates and visualised with a) UV-light and b) vanillin/sulphuric acid and heating.

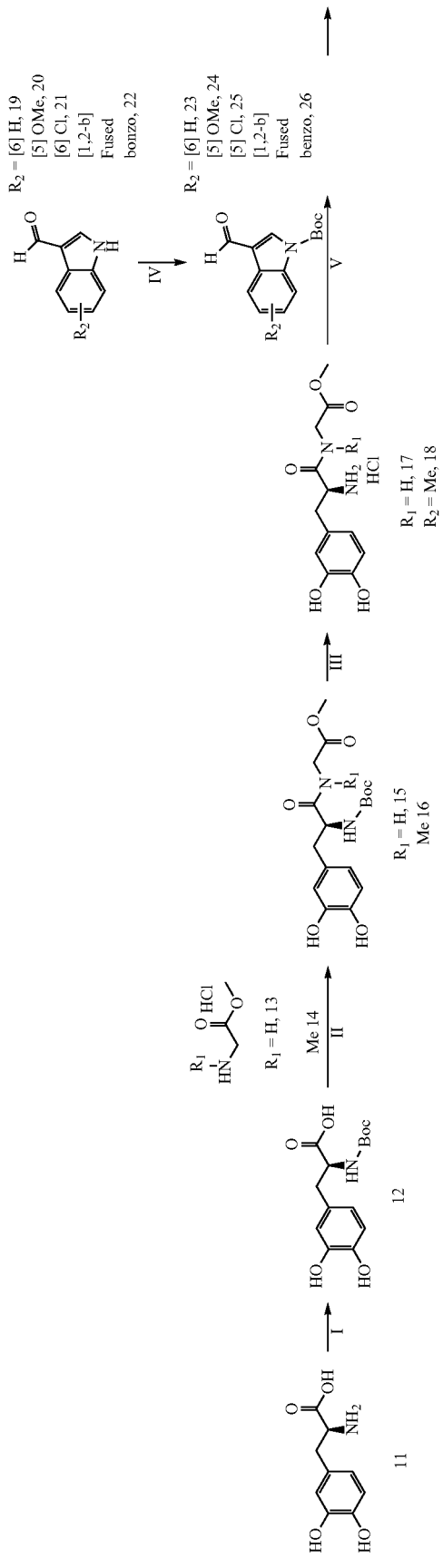
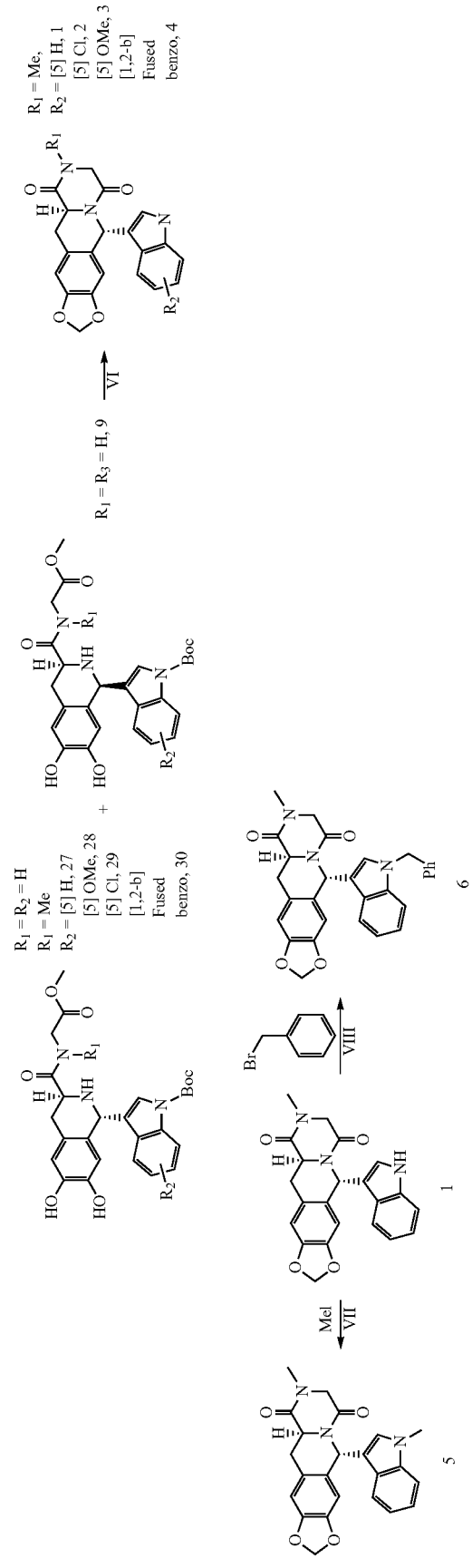

Procedure for the Synthesis of Intermediate (12). (Step I)

To a solution of L-Dopa (11) (1 eq) in dioxane (resulting in a 0.6 M solution of L-Dopa (11)) was added 1M NaOH (1.1 eq), $H_2O$ (55 eq) and $Boc_2O$ (1.1 eq) dissolved in dioxane (resulting in a 2.8 M solution of $Boc_2O$). After 30, 60 and 120 min the pH was adjusted to 10 by the addition of 1 M NaOH. The solution was stirred at rt on. The solution was conc. under reduced pressure, the pH was adjusted to ~2 by the addition of 1 M HCl and extracted with EtOAc×2. The pooled org. phases were dried over $Na_2SO_4$ filtered and evaporated. The product was not further purified.

General Procedure for the Synthesis of Intermediate (15) and (16). (Step II)

To a suspension of the carboxylic acid (12) (1 eq.) and the amine (eg. (13), (14)) (1.1 eq) in $CH_2Cl_2$ (resulting in a 0.03 M solution of the carboxylic acid (11)) was added $Et_3N$ (3.5 eq) and the resulting solution was cooled to 0° C. Bop-Cl (1.16 eq) followed by $NaHCO_3$ (2.1 eq) was added and the suspension was stirred at rt on. The volatiles were evaporated and the residual was separated between EtOAc and 1 M HCl. The org. phase was washed with sat. (aq) $NaHCO_3$, brine, dried over $Na_2SO_4$, filtered and evaporated. The residue was purified by flash column chromatography (EtOAc/Pet. ether (60-80) as eluent).

General Procedure for the Synthesis of Intermediate (17) and (18). (Step III)

To a stirred suspension of the Boc protected primary amine (eg. (15), (16)) was added 2 M HCl in $Et_2O$ (resulting in a 0.1 M suspension of the protected amine (eg. (15), (16)) at 0° C. The suspension was stirred at 0° C. for 1 h. The suspension was filtered off, washed with ice-cold $Et_2O$, dissolved in MeOH and evaporated. The product wasn't further purified.

General Procedure for the Synthesis of Intermediate (23), (24), (25) and (26). (Step IV)

To a solution of the indole derivative (eg. (19), (20), (21), (22)) (1 eq) in dry THF (resulting in a 0.05 M solution of the indole derivative (eg. (19), (20), (21), (22))) were $Boc_2O$ (1.5 eq) followed by DMAP (0.3 eq) added. The solution was stirred at rt for 6 h. The solution was diluted with $H_2O$, the volatiles evaporated and the residual extracted with EtOAc× 2. The pooled org. phases were washed with brine, dried over $Na_2SO_4$, filtered and evaporated. The product wasn't further purified.

General Procedure for the Synthesis of Intermediate/Substance (9), (10), (27), (28), (29) and (30). (Step V)

To a solution of the primary amine (eg. (17) or (18)) (1 eq) in AcOH (resulting in a 0.07 M solution of the primary amine (eg. (17) or (18))) was added 3 eq NaOAc and 1 eq aldehyde (eg. (23), (24), (25), (26)). The mixture was stirred at rt on. The mixture was neutralized by the addition of sat. (aq) $NaHCO_3$ and extracted 3 times with $CH_2Cl_2$. The pooled org. phases were washed with brine, dried over $Na_2SO_4$ filtered and evaporated. The residue was filtered on $SiO_2$ (EtOAc as eluent)/purified by flash column chromatography (EtOAc as eluent).

General Procedure for the Synthesis of Substance (1), (2), (3) and (4). (Step VI)

To a mixture of the tetrahydroisoquinoline derivative (eg. (27), (28), (29), (30)) (1 eq) and $Cs_2CO_3$ (1.5 eq) in freshly distilled DMF (resulting in a 0.5 M solution of the tetrahydroisoquinoline derivative (eg. (27), (28), (29), (30)) was added $BrCH_2Cl$ (1.5 eq). The mixture was heated at 150° C. for 2.5 h. The mixture was filtered, diluted with EtOAc, washed with $H_2O×2$, brine, dried over $Na_2SO_4$, filtered and evaporated. The residue was purified by flash column chromatography (EtOAc/Pet. ether (60-80) as eluent).

Procedure for the Synthesis of Substance (5). (Step VII)

To a solution of (1) (1 eq) in freshly distilled DMF (resulting in a 0.4 M solution of (1)) at 0° C. was added NaH (1.2 eq), the mixture was stirred at 0° C. for 10 min after which MeI (1.2 eq) was added. The solution was stirred at rt on. $H_2O$ was added and the mixture was extracted with EtOAc×3. The pooled org. phases were washed with $H_2O$, brine, dried over $Na_2SO_4$, filtered and evaporated. The residue was purified by flash column chromatography (EtOAc/Pet. ether (60-80) as eluent).

Procedure for the Synthesis of Substance (6). (Step VIII)

To a solution of (1) (1 eq) in freshly distilled DMF (resulting in a 0.5 M solution of (1)) at 0° C. was added NaH (1.2 eq), the mixture was stirred at 0° C. for 10 min after which benzyl bromide (1.2 eq) was added. The solution was stirred at rt for 4 h. $H_2O$ was added and the mixture was extracted with EtOAc×3. The pooled org. phases were washed with $H_2O$, brine, dried over $Na_2SO_4$, filtered and evaporated. The residue was purified by flash column chromatography (EtOAc/Pet. ether (60-80) as eluent).

Example 1

Also Referred to Herein as "Substance X"

(5S,9aS)-5-(1H-Indol-3-yl)-8-methyl-7,8,9a,10-tetrahydro-5H-1,3-dioxa-5a,8-diaza-cyclopenta[b]anthracene-6,9-dione (alternative name: (2S,8S)-2-(1H-indol-3-yl)-6-methyl-13,15-dioxa-3,6-diazatetracyclo[8.7.0.0$^{3,8}$.0$^{12,16}$]heptadeca-1(10),11,16-triene-4,7-dione (1))

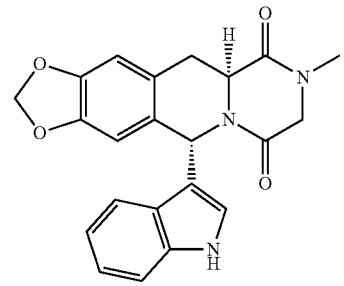 [SMILES: CN1CC(=O)N2[C@H](c3c[nH]c4ccccc34)c3cc4c(cc3C[C@H]2C1=O)OCO4]

(a) N-Boc Protected L-Dopa (2)

To a solution of 5.004 g (25.4 mmol) L-Dopa (1) in 40 ml dioxane and 25 ml $H_2O$, 28 ml (28 mmol) 1 M NaOH and 6.0893 g (27.9 mmol) $BOC_2O$ dissolved in 8 ml dioxane was added. The resulting solution was stirred at r.t. After 30 minutes the pH was adjusted to 10 by the addition of 1 M NaOH. The pH was again adjusted to 10 after 1 h and after 7.5 h. After the last pH adjustment the solution was stirred overnight. The volatiles were evaporated and resulting water phase was the adjusted to pH 2 and extracted with 3×100 ml EtOAc. The pooled organic phases were washed with 150 ml water, 150 ml brine, dried over $Na_2SO_4$, filtered and evaporated to give 7.6 g (25.4 mmol, 100%) N-Boc-protected L-Dopa (2).

(b) N-Boc-{[(S)-2-Amino-3-(3,4-dihydroxy-phenyl)-propionyl]-methyl-amino}-acetic acid methyl ester (3)

5.0341 g (16.9 mmol) (2) and 2.6002 g (18.6 mmol) sarcosine methyl ester hydrochloride were suspended in 500 ml CH₂Cl₂. 8.3 ml (59.5 mmol) Et₃N was added and the mixture was cooled to 0° C. 5.0118 g (19.7 mmol) Bop-Cl followed by 2.9991 g (35.7 mmol) NaHCO₃ were added and the mixture was stirred at r.t. overnight. The volatiles were evaporated and the residue was separated with 400 ml EtOAc and 400 ml 1 M HCl (aq.). The organic phase was washed with 400 ml sat (aq.) NaHCO₃, 200 ml brine, dried over Na₂SO₄, filtered and evaporated. Flash chromatography (Pet. ether:EtOAc, 1:4) gave 1.9425 g (5.1 mmol, 30%) (3).

(c) {[(S)-2-Amino-3-(3,4-dihydroxy-phenyl)-propionyl]-methyl-amino}-acetic acid methyl ester. hydrochloric acid (4)

To 1.514 g (3.96 mmol) (3) 42 ml 2M HCl in Et₂O was added at 0° C. The resulting suspension was stirred at 0° C. for 1 h. The suspension was filtered off and washed with ice cold Et₂O, re-dissolved in a minimal amount MeOH and evaporated. The substance was not further purified (0.897 g (2.8 mmol, 71%) (4)).

(d) N-Boc-indole-3-carboxaldehyde 0.8754 g (6 mmol) indole-3-carboxaldehyde was taken up in 170 ml freshly distilled THF, 2.0323 g (9.3 mmol) Boc₂O followed by 0.2006 g (1.6 mmol) DMAP were added and the mixture was stirred at r.t for 4 h. 75 ml H₂O was added and the volatiles were evaporated. The residue was extracted with 2×75 ml EtOAc. The pooled organic phases were washed with 75 ml brine, dried over Na₂SO₄, filtered and evaporated. This gave 1.4790 g (6 mmol) Boc-protected indole-3-carboxaldehyde.

(e) (6S,11aS)-8,9-Dihydroxy-6-(1-Boc-1H-indol-3-yl)-2-methyl-2,3,11,11a-tetrahydro-6H-pyrazino[1,2-b]isoquinoline-1,4-dione (5)

0.897 g (2.8 mmol) (4) was dissolved in 56 ml AcOH, 0.6969 g (8.4 mmol) NaOAc and 0.6923 g (2.8 mmol) Boc protected indole-3-carboxaldehyde was added. The mixture was stirred at room temperature overnight. The reaction mixture was divided in two and each of the halves were neutralized by the addition of sat (aq.) NaHCO₃ (pH 8), extracted with 150 ml CH₂Cl×3. The pooled organic phases were washed with 200 ml brine, dried over Na₂S04, filtered and evaporated. Flash chromatography (EtOAc) gave 0.665 g (1.4 mmol, 50%) (5).

(f) (5S,9aS)-5-(1H-Indol-3-yl)-8-methyl-7,8,9a,10-tetrahydro-5H-1,3-dioxa-5a,8-diaza-cyclopenta[b]anthracene-6,9-dione (6)

0.665 g (1.4 mmol) (5) and 0.6853 g (2.1 mmol) Cs₂CO₃ was suspended in 3.3 ml freshly distilled DMF. 0.140 ml (2.1 mmol) BrCH₂Cl was added and the mixture was heated at 150° C. for 1.5 h. The heat source was removed and the mixture was allowed to cool to r.t. after which the mixture was filtered and separated with 100 ml EtOAc and 100 ml H₂O. The water phase was extracted with 2×100 ml EtOAc. The pooled organic phases were washed with 150 ml brine, dried over Na₂SO₄, filtered and evaporated. Flash chromatography (Pet. ether:EtOAc, 1:4) gave 0.167 g (0.43 mmol, 31%) (6).

¹H NMR (400 MHz, DMSO-d₆): δ 11.07 (bs, 1H), 7.54 (d, J=7.9 Hz, 1H), 7.36 (d, J=8.1 Hz, 1H), 7.09 (t, J=7.4 Hz, 1H), 6.98 (t, 7.5 Hz, 1H), 6.94 (1H), 6.84 (s, 1H), 6.74 (s, 1H), 6.71 (s, 1H), 5.99 (s, 1H), 5.98 (s, 1H), 4.21 (d, J=17.5 Hz, 1H), 4.05 (dd, J₁=11.9 Hz J₂=4.4 Hz, 1H), 3.99 (d, J=17.64 Hz, 1H), 3.10 (m, 2H), 2.78 (s, 3H)

m/z calc. for C₂₂H₂₀N₃O₄(M+H)⁺: 390.1448. found: 390.1454.

Example 2

Also Referred to Herein as "Analogue 1"

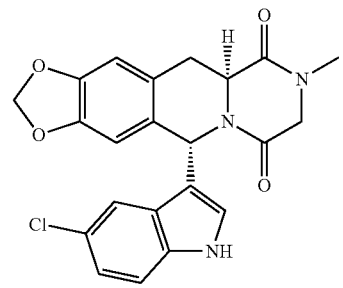

2

(2S,8S)-2-(5-chloro-1H-indol-3-yl)-6-methyl-13,15-dioxa-3,6-diazatetracyclo-[8.7.0.0³,⁸.0¹²,¹⁶]heptadeca-1(10),11,16-triene-4,7-dione (2)

¹H NMR (400 MHz, CD₂Cl₂): δ 8.37 (bs, 1H), 7.79 (d, J=2.1 Hz, 1H), 7.35 (d, J=8.7 Hz, 1H), 7.19 (dd, J₁=8.7 Hz J₂=2.0 Hz, 1H), 7.08 (s, 1H), 6.79 (d, J=2.5 Hz, 1H), 6.72 (s, 1H), 6.62 (1H), 5.99 (d, J=1.3 Hz, 1H), 5.97 (d, J=1.3 Hz, 1H), 4.29 (dd, J₁=12.6 J₂=4.3 Hz, 1H), 4.13 (d, J=17.7 Hz, 1H), 4.01 (d, J=17.7 Hz, 1H), 3.31 (dd, J₁=16.3 Hz J₂=4.2 Hz, 1H), 3.01 (dd, J₁=16.2 Hz J₂=12.5 Hz, 1H), 2.92 (s, 3H)

m/z calc. for C₂₂H₁₈ClN₃O₄Na (M+Na)⁺: 446.0878. found: 446.0884.

Example 3

Also Referred to Herein as "Analogue 2"

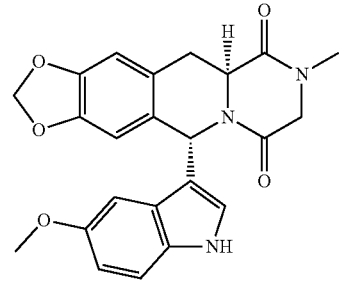

3

(2S,8S)-2-(5-methoxy-1H-indol-3-yl)-6-methyl-13,15-dioxa-3,6-diazatetracyclo[8.7.0.0³,⁸.0¹²,¹⁶]heptadeca-1(10),11,16-triene-4,7-dione (3)

¹H NMR (400 MHz, CDCl₃): δ 8.73 (bs, 1H), 7.34 (m, 1H), 7.24 (d, J=8.8 Hz, 1H), 7.11 (s, 1H), 6.87 (dd, J₁=8.8 Hz J₂=2.6 Hz, 1H), 6.62 (m, 3H), 5.93 (d, J=1.3 Hz, 1H), 5.91 (d, J=1.3 Hz, 1H), 4.35 (dd, J₁=16.3 Hz J₂=4.3 Hz, 1H), 4.08 (m,

1H), 3.98 (d, J=17.7 Hz, 1H), 3.85 (s, 3H), 3.31 (dd, $J_1$=16.3 Hz $J_2$=4.3 Hz, 1H), 2.94 (m, 1H), 2.88 (s, 3H)

m/z calc. for $C_{23}H_{21}N_3O_5Na$ (M+Na)$^+$: 442.1373. found: 442.1379.

Example 4

Also Referred to Herein as "Analogue 3"

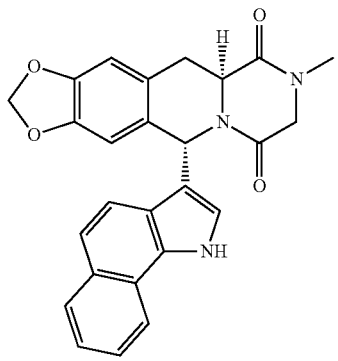

4

(2S,8S)-6-methyl-2-{1H-naphtho[1,2-b]pyrrol-3-yl}-13,15-dioxa-3,6-diazatetracyclo[8.7.0.0$^{3,8}$.0$^{12,16}$]heptadeca-1(10),11,16-triene-4,7-dione (4)

$^1$H NMR (400 MHz, CD$_2$Cl$_2$): δ 9.818 (bs, 1H), 8.09 (d, J=8.2 Hz, 1H), 7.89 (d, J=8.1, 1H), 7.82 (d, J=8.7 Hz, 1H), 7.49 (t, J=8.1 Hz, 1H), 7.49 (d, J=8.8 Hz, 1H), 7.39 (t, J=8.0 Hz, 1H), 7.16 (s, 1H), 6.69 (d, J=2.1 Hz, 1H), 6.60 (s, 1H), 6.59 (d, J=3.9 Hz, 1H), 5.92 (d, J=1.1 Hz, 1H), 5.91 (d, J=1.1 Hz, 1H), 4.35 (dd, $J_1$=12.4 Hz $J_2$=4.2 Hz, 1H), 4.11 (d, J=17.7 Hz, 1H), 3.96 (d, J=17.8 Hz, 1H), 3.29 (dd, $J_1$=16.4 Hz $J_2$=4.3 Hz, 1H), 3.00 (dd, $J_1$=16.1 Hz, $J_2$=12.5 Hz, 1H), 2.88 (s, 3H)

m/z calc. for $C_{26}H_{22}N_3O_4$(M+H)$^+$: 440.1605. found: 440.1610

Example 5

Also Referred to Herein as "Analogue 4"

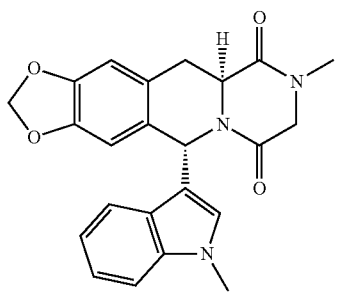

5

(2S,8S)-6-methyl-2-(1-methyl-1H-indol-3-yl)-13,15-dioxa-3,6-diazatetracyclo-[8.7.0.0$^{3,8}$.0$^{12,16}$]heptadeca-1(10),11,16-triene-4,7-dione (5)

$^1$H NMR (400 MHz, CD$_2$Cl$_2$): δ 7.74 (d, J=8.0 Hz, 1H), 7.33 (d, J=8.2 Hz, 1H), 7.26 (dt, $J_1$=8.2 Hz $J_2$=1.1 Hz, 1H), 7.12 (m, 2H), 6.73 (s, 1H), 6.65 (s, 1H), 6.62 (s, 1H), 5.99 (d, J=1.1 Hz, 1H), 5.97 (d, J=1.1 Hz, 1H), 4.34 (dd, $J_1$=12.4 Hz, $J_2$=4.2 Hz, 1H), 4.11 (d, J=17.7 Hz, 1H), 3.96 (d, J=17.7 Hz, 1H), 3.71 (s, 3H), 3.32 (dd, $J_1$=16.3 Hz $J_2$=4.3 Hz, 1H), 3.01 (dd, $J_1$=16.2 Hz $J_2$=12.6 Hz, 1H), 2.89 (s, 3H)

m/z calc. for $C_{23}H_{22}N_3O_4$(M+H)$^+$: 404.1605. found: 404.1610

Example 6

Also Referred to Herein as "Analogue 5"

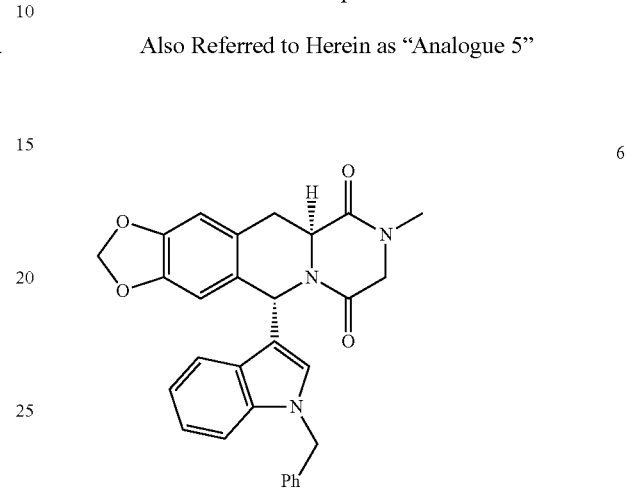

6

(2S,8S)-2-(1-benzyl-1H-indol-3-yl)-6-methyl-13,15-dioxa-3,6-diazatetracyclo-[8.7.0.0$^{3,8}$.0$^{12,16}$]heptadeca-1(10),11,16-triene-4,7-dione (6)

$^1$H NMR (400 MHz, CD$_2$Cl$_2$): δ 7.77 (d, J=7.9 Hz, 1H), 7.20 (m, 9H), 6.77 (s, 1H), 6.72 (s, 1H), 6.67 (s, 1H), 5.98 (d, J=1.1 Hz, 1H), 5.97 (d, J=1.1, 1H), 5.27 (s, 2H), 4.34 (dd, $J_1$=12.4 Hz, $J_2$=4.3 Hz, 1H), 4.12 (d, J=17.7 Hz, 1H), 3.98 (d, J=17.7 Hz, 1H), 3.32 (dd, $J_1$=16.3 Hz, $J_2$=4.4 Hz, 1H), 3.01 (dd, $J_1$=16.3 Hz $J_2$=12.5 Hz, 1H), 2.92 (s, 3H)

m/z calc. for $C_{29}H_{25}N_3O_4Na$ (M+Na)$^+$: 502.1737. found: 502.1743

BIOLOGICAL EXAMPLES

Biological Example A

Materials and Methods

Materials

Substance X was dissolved in 100% DMSO diluted to 5% in PBS buffer.

Xenograft Mouse Model of Tumor Growth and Metastasis

Athymic NMRI nude mice between 6-8 weeks old (Taconic; Bomholt, Denmark) were used. Prostate cancer xenograft mouse model was created by implanting hormone-independent PC3 tumor cells subcutaneously into athymic nude mice as previously described (Wegiel B, Bjartell A, Tuomela J, et al.: Multiple cellular mechanisms related to cyclin A1 in prostate cancer invasion and metastasis. Journal of the National Cancer Institute 100: 10221036, 2008).

PC-3 cells were purchased from American Type Culture Collection (Manassas, V A) and cultured in RPMI-1640 supplemented with 10% Fetal Bovine Serum. PC-3 cells at $1\times10^6$/per mouse were used. The mice were divided into three groups (6 mice per group). The first group allowed tumors to grow between 170-400 mm$^3$ in size before starting the treatment. The second group allowed tumors to grow between 550-650 mm³ in size before starting the treatment. The third group allowed tumors to grow between 700-800 mm³ in size before starting the treatment. The tumor diameters were measured twice weekly using calipers. The tumor volumes were calculated using an equation of a*(b2/2) where a and b represent the length and width of the tumor, respectively.

The treatment of the compound of Example 1 (also referred to herein as "Substance X") or PBS containing 5% DMSO (vehicle) as Control was started when tumors reached the desired size as described above. In the first experimental setting, Substance X was administered intravenously once every other day. In the second experimental setting, Substance X was administrated orally once every other day. Tumor growth was assessed periodically as described in Results. The mice were sacrificed after treatment by euthanization via isofluorene inhalation. Lymph node, liver, lung, spleen and femurs were removed from each mouse. Half of the tumor tissues were used for histology and immunohistochemical analysis. For histology analysis, tissues were fixed in 4% paraformaldehyde and embedded in paraffin. The sections were stained with hematoxylineosin (H&E) or imunohistochemical stained with antibodies and analyzed under an optical microscope. The other half of the tissues were used for protein analysis and thus were snapfrozen in liquid nitrogen. The body weights of the mice on the first and last day of the treatment were collected and compared. Tumor invasion and metastasis were examined in various tissues from the sacrificed mice.

For a comparison study, mice with tumors at 190-250 mm³ in size were treated with the cytotoxic drug Etoposide (Sigma) at a dose of 20 mg/kg via IV injection once every other day. The tumor size was measured as described in the Results. Three mice were treated with Etoposide or the vehicle as Control. The mice were sacrificed and the tissues were collected as described above.

Basic Toxicity Study

For the assessment of toxicity of Substance X, healthy mice were treated with Substance X by intravenous injection at a dose of 100 mg/kg or 200 mg/kg once every other day for 13 days. Body weight of each mouse was measured periodically from Day 1 to Day 13 of the treatment. Cage-side observations including: mortality, moribundity, food consumption and activities were performed once every other day. Blood samples were taken on Day 1 and Day 13 for measurement of blood cell counts. To assess toxicity of Substance X on mice with tumors, mice bearing subcutaneous PC-3 tumors were treated with Substance X at a high dose of 200 mg/kg once every other day for 19 days. Body weight was measured and cage-side observations were performed once every other day. Lymph node, liver, lung, spleen and femurs were removed from each mouse and were examined. Toxicity of Substance X was also assessed in tumor-bearing mice treated with 80 mg/kg of Substance X daily as described above.

Immunohistochemistry and Quantification of Angiogenesis

Immunohistochemistry on tumor tissues was performed as previously described (Wegiel B, Bjartell A, Ekberg J, Gadaleanu V, Brunhoff C and Persson J L: A role for cyan AI in mediating the autocrine expression of vascular endothelial growth factor in prostate cancer. Oncogene 24: 6385-6393, 2005) by using antibodies to human CD-31 (Dako, Goistrup, Denmark A/S). Antirabbit peroxidase-conjugated secondary antibodies were applied. Diaminobenzidine colorimetric reagent solution (Dako) was used. Slides were counterstained with hematoxylin (Sigma, St. Louis, Mo.). The specimens were viewed with an Olympus BX5I microscope at a magnification of 20× or 40×. For analysis of tumor angiogenesis, tumor sections stained with antibody against CD3I were examined and quantified. Regions of high vascular density within the tumors were examined. The number of CD31-positive pixels per microscopic field was recorded. At least two sections per tumor and three views per section were determined.

RESULTS

Safety in Basic Toxicity Study

Basic safety study of Substance X was first performed on healthy mice without tumors to test if a high dose of 100 mg/kg at once every other day regimen was safe. As shown in FIG. 1 A, there was no significant change in body weight throughout the 13 day treatment period with high dose of Substance X. The cage-side observations showed no abnormality on food consumption and daily activities, or any observable toxic effect for 13 days. Analysis of livers and kidney was conducted and no abnormality in histology in these organs could be detected (data not shown). These basic toxicity tests showed that Substance X is safe at a high dose in healthy mice.

The mice were treated with 200 mg/kg of Substance X once every other day for a long period of time of 13 days. As shown in FIG. 1 B, the body weights of the tumor-bearing mice were steady throughout the study period. The cage-side observations showed no abnormality on food consumption and daily activities, or any observable toxic effect. Analysis of livers and kidney was conducted and no abnormality in histology in these organs could be detected (data not shown).

We then tested the high dose of Substance X in PC-3 xenograft mice, thereby mimicking its effect on prostate cancer patients. We generated mouse xenograft of human PC-3 tumors by subcutaneous implantation of tumor cells into nude mice. We further tested safety of the dose of 40 mg/kg which generated significant anti-tumor activity in the xenograft mouse model. The daily treatment of tumor-bearing mice with this dose may suggest the safety of Substance X for cancer treatment. The body weights of tumor-bearing mice treated with Substance X daily for 30 days remained constant throughout the period of treatment (data not shown). The cage-side observations showed no abnormality on food consumption and/or daily activities, or any other observable toxic effect. Analysis of livers and kidney was conducted and no abnormality in histology in these organs could be detected (data not shown).

Inhibition of Tumor Growth in Xenograft Animal Model

We created a prostate cancer xenograft mouse model to study the effect of Substance X on tumor growth and metastasis in viva Metastatic prostate cancer PC-3 cells were injected subcutaneously into the right flank of each mouse to create a xenograft mouse model. When the tumors were grown to 190-240 mm³ in size, the mice were treated intravenously with Substance X at 20 mg/kg or the vehicle as Control for 21 days. The tumors in the Control group treated with vehicle alone grew to exponentially large size after 21 days, while tumor shrank in the mice treated with Substance X. This suggests a significant inhibitory effect of Substance X on tumor growth in xenograft mice in viva Inhibition of Tumor Growth and Invasion in Xenograft Mice with Large and Invasive Tumors Next, we assessed the effect of Substance X on tumor growth and invasion in mice bearing larger tumors. We have previously found that PC-3 tumors grown into 400 mm³ in size could become metastatic and the tumor cells would invade into lymph node, liver or lung. To test if Substance X is able to control aggressive tumor growth, we allowed the tumor transplants to grow approximately 500-600 mm$^3$ in size and then started to treat the mice with 40 mg/kg Substance X or the solvent as Control by intravenous injection. While the large tumors in the Control group continued to grow rapidly, the tumors in the Substance X treated mice did not grow but showed a slight decrease in size on day 20 (FIG. 2).

We then tested the effect of Substance X on the large and invasive tumors for longer period of time. We divided the mice into two groups, one group was treated with 40 mg/kg Substance X by intravenous injection for 30 days, while the other group was treated with Substance X by the same treatment regimen for 20 days. On day 21, the group 2 mice were treated with 40 mg/kg Substance X by oral administration. The result showed that the tumor growth in Substance X treated mice was inhibited throughout the treatment period and the tumors shrank significantly at the end of the treatment. In contrast, the tumors in the Control group grew exponentially and became metastasized. In the second treatment group, the mice treated with Substance X by oral administration had slightly larger tumor size than the mice treated by continuous intravenous injection, suggesting that Substance X is orally bioavailable, yet the oral bioavailability is lower than intravenous injection. We performed histology and immunohistochemical analysis and no infiltration of tumor cells into secondary sites could be detected in any of these mice at the end of the study. In contrast, tumors in the Control mice were found to have metastasized into lymph nodes (data not shown).

We also treated the mice by oral administration of Substance X throughout the treatment period. As shown in FIG. 3, Substance X given to the mice via oral administration was able to inhibit the tumor growth, although the effect was not as strong as intravenous injection.

Comparison of Effect of Etoposide and Substance X on Tumor Growth in Xenograft Mice To compare the effect of Substance X with a cytotoxic drug widely used to treat invasive tumors, we tested the effect of Etoposide at 20 mg/kg by intravenous injection (IV) on PC-3 mice bearing tumors grown to approximately 250 mm$^3$ in size. As shown in FIG. 4, the tumors in the Control group grew to exponentially large size after 14 days. In contrast, tumors in the Etoposide treatment group grew slowly. More importantly, Substance X showed stronger inhibitory effect on tumors as compared to Etoposide.

Effect of Substance X on VEGF and VEGF Receptor 2 Expression in Tumor Xenograft Mice We examined the expression of VEGF and VEGFR2, the important angiogenic factors that can promote tumor vasculatures and are required for tumor invasion. Immunohistochemical analysis was performed on tumors dissected from Control mice or mice treated with Substance X. As compared to the Control, the expression of VEGF and VEGFR2 was significantly down-regulated in tumors treated with Substance X (FIG. 5). This suggests that Substance X may be a VEGF inhibitor that targets VEGF signalling pathways.

Effect of Substance X on Tumor Histology and Vascularisation of Tumors in Xenograft Mice We also characterized tumor histology by VEGF receptor 2 staining in mice treated with vehicle or Substance X. Side-by-side comparison of the sections containing the whole tumors from Control mice and Substance X treated mice clearly revealed differences in tumor size and morphology between the two groups (FIG. 6A). The size of the tumors from mice treated with Substance X appeared to be smaller than that from the Control mice. Interestingly, there were large empty areas in tumors treated with Substance X, suggesting an ongoing tumor reduction may be associated with the clearance of dead tumor cells. These results further confirmed that Substance X is capable of inhibiting growth in large and invasive tumors.

We then measured the expression of CD31, a protein expressed in tumor vasculatures and important for tumor invasion, in tumors treated with Substance X by immunohistochemical analysis (FIG. 6B). We determined the extent of tumor vascularisation by quantifying CD31 expression and CD31 positive vessels in the tumors including the edge and the centre areas of the tumors. There was a statistically significant decrease in CD31 expression and the number of CD31-expressing vessels in tumors treated with Substance X as compared with that of the Control tumors (FIG. 6C). This result suggests that Substance X may inhibit tumor growth and invasion by preventing the vascularisation of aggressive PC-3 tumors.

Biological Example B

Materials and Methods

Chemicals

All new synthesized compounds and Etoposide were first dissolved in 100% DMSO at initial concentration of 100 mM, and then diluted at final concentration of 200 uM in culture medium. Commercial form of Avastin (25 mg/ml) was diluted to appropriate concentrations in culture medium.

Cell Culture

Hormone-independent and metastatic PC-3 prostate cancer cells were purchased from the American Type Culture Collection (Manassas, Va., USA) and cultured in RPMI-1640 supplemented with 10% fetal bovine serum. Etoposide was purchased from Sigma, Avastin from Roche.

Cell Proliferation Assay and 1050 Determination

For cell counting a total of 6×10$^4$ cells at a density of 0.3×10$^6$/ml were seeded in 96-well plate. The cells were treated with compounds, Etoposide or Avastin as positive controls at 1 uM, 5 uM, 10 uM, 20 uM, 50 uM, 100 uM for 48 hours. For Avastin 5 uM, 20 uM and 50 uM concentrations were used. The cells were labeled with trypan blue and the viable cells were quantified.

The effect of analogues on proliferation of PC-3 cells was determined using a nonradioactive BrdU-based cell proliferation assay kit (Roche, Germany) according to manufacturer's protocol. Etoposide and Avastin were used as positive controls. Briefly, 2×10$^3$ cells were cultured in a 96/well plate in RPMI-1640 medium containing 10% FBS for 48 hours, including labeling with BrdU for 18 hours. BrdU incorporation into the cellular DNA was determined by measuring the absorbance at 450 nm and 690 am on an ELISA plate reader.

Annexin V-Apoptosis Assay

Cells were treated with 50 uM and 100 uM compounds and Etoposide for 48 hours, harvested, washed with PBS and resuspended in binding buffer (0.01 M HEPES pH 7.4, 0.14 M NaCl, 2.5 M mM CaCl$_2$) (BD Bioscience, san Jose, Calif., USA), stained with APS-conjugated annexin V and 7-AAD (BD Bioscience). The cells were incubated for 15 min at room temperature in the dark, and the rate of apoptosis was measured by flow cytometry (Calibur, BD) and analyzed using FCS Express Professional software (De NoVo software, CA, USA).

Cell Cycle Analysis

Cells were harvested after the treatment, then fixed in ice-cold 70% EtOH. Cells then were washed with PBS and incubated in DNA staining buffer, containing 1 mg/ml sodium citrate (Sigma), 0.1 mg/ml propidium iodide (Sigma), 3 ul/ml TritonX-100, 0.02 mg/ml RNaseA (Sigma) for 30 min at 4° C. The cell cycle profiles were measured in a FACS Calibur cytofluorometer (BD) and analyzed using FCS Express Professional (De NoVo software, CA, USA) and Multicycle (Phoenix Flow Systems, Inc., CA, USA) softwares.

RESULTS

Evaluation of the Effect of Compound X and its Analogues on the Growth of Metastatic Prostate Cancer PC-3 Cells A. Comparison of IC50 Values of Lund University and Enamine Synthesized Compound X.

There is no difference between different batches of Compound X in efficacy. Both of them induced dose-dependent inhibition of cell growth with statistically significant cell number reduction 5 uM. The 1050 for growth inhibition was calculated to be 30 uM (see FIG. 7).

B. Analogue 1 Effect on PC-3 Cells Growth

Analogue 1 with calculated 1050 for cell growth 36 uM. The statistically significant cell growth inhibition started between 10 um and 20 uM (see FIG. 8).

C. Analogue 2 Effect on PC-3 Cells Growth

Analogue 2 significant growth inhibition started from 5 uM concentration. Determined IC50 for cell growth was 60 uM (see FIG. 9).

D. Analogue 3 Effect on PC-3 Cells Growth

Analogue 3 showed effect from 5 uM, as Compound X and IC 50 was 32 uM (see FIG. 10).

E. Analogue 4 Effect on PC-3 Cells Growth

Analogue 4 cell treatment showed statistically significant cell growth inhibition from 10 um to 100 uM. Calculated IC50 was 30 uM (see FIG. 11).

F. Analogue 5 Effect on PC-3 Cells Growth

Analogue 5 treatment of the PC-3 cells resulted in cell reduction (FIG. 12).

BrdU Based Cell Proliferation Assay

Figure 1:
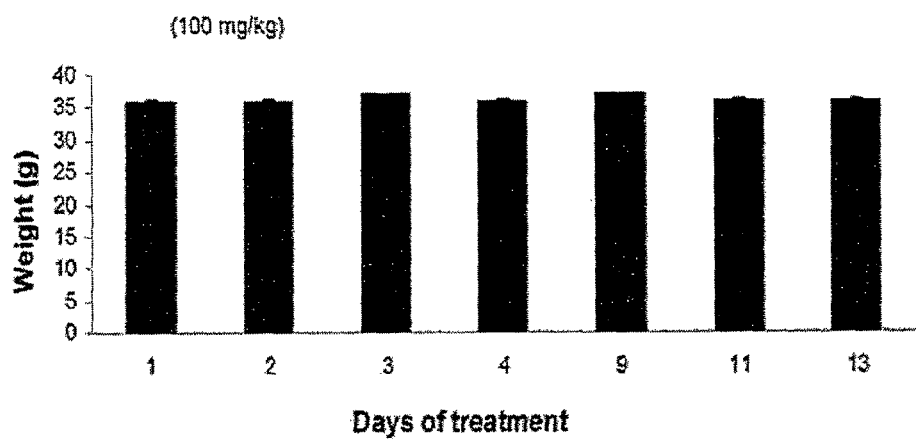
Figure 1:
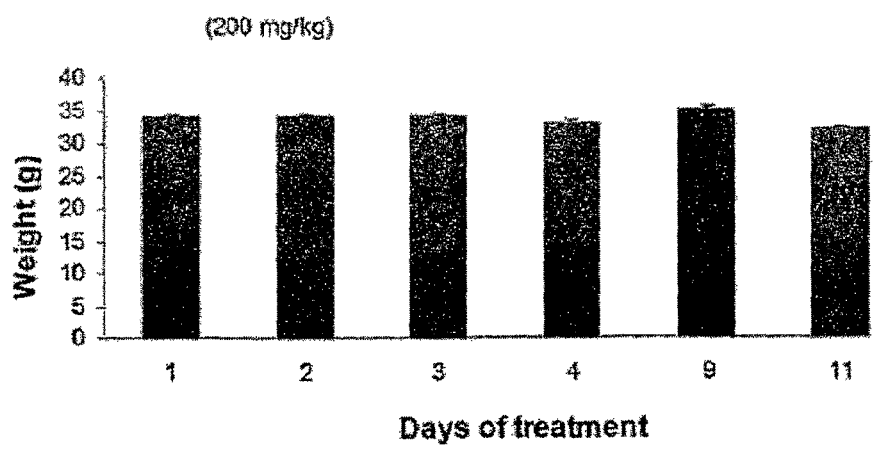
Figure 2:
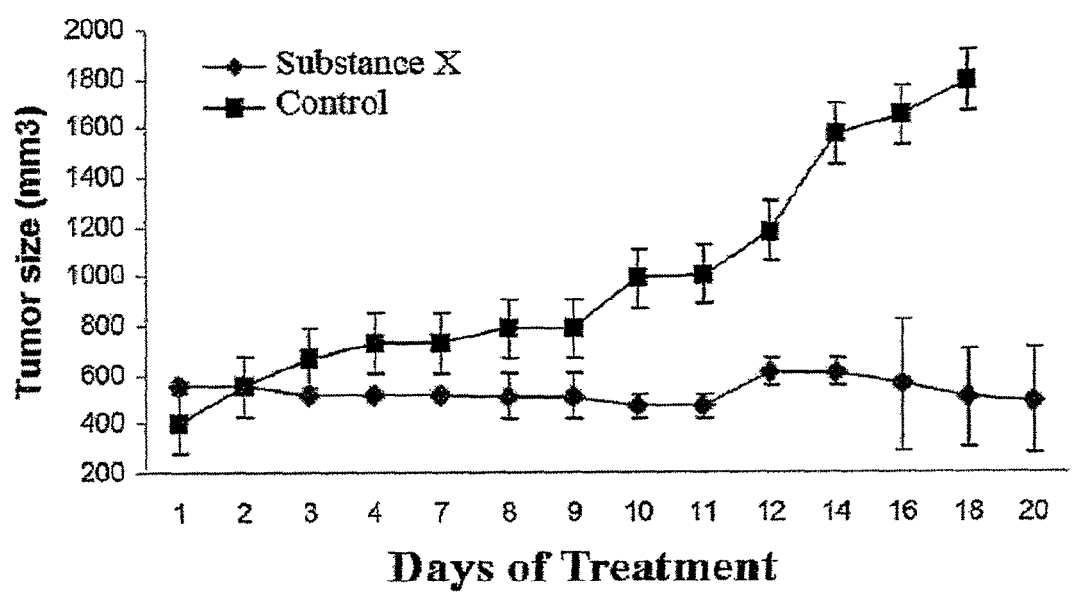
Figure 3:
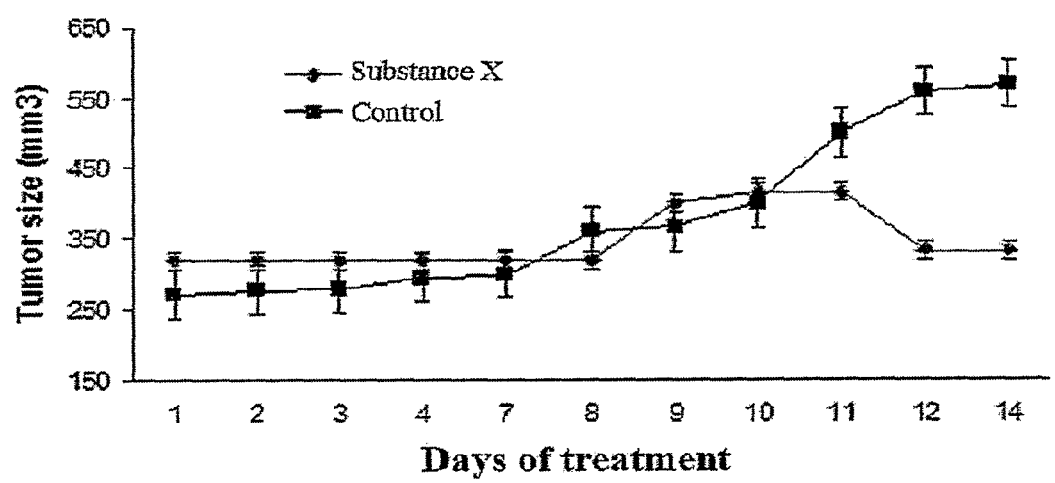
Figure 4:
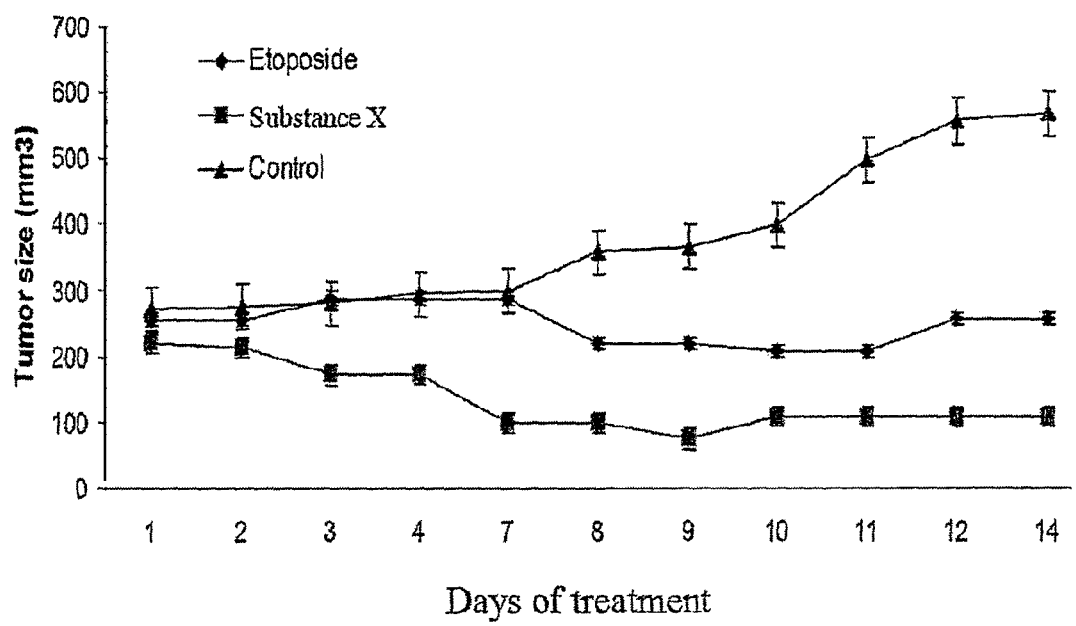
Figure 5:
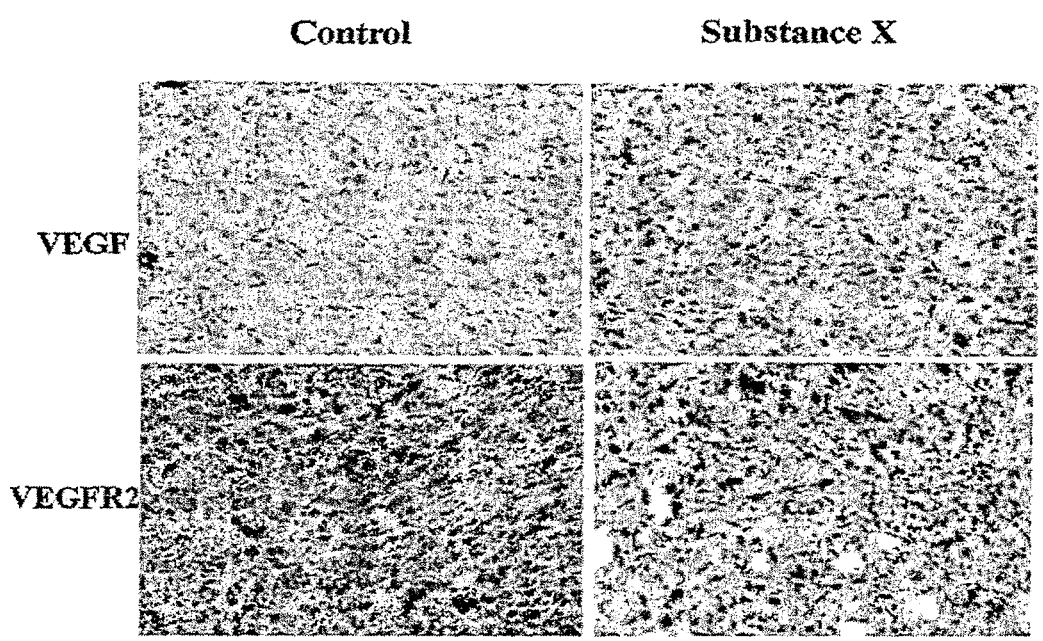
Figure 6:
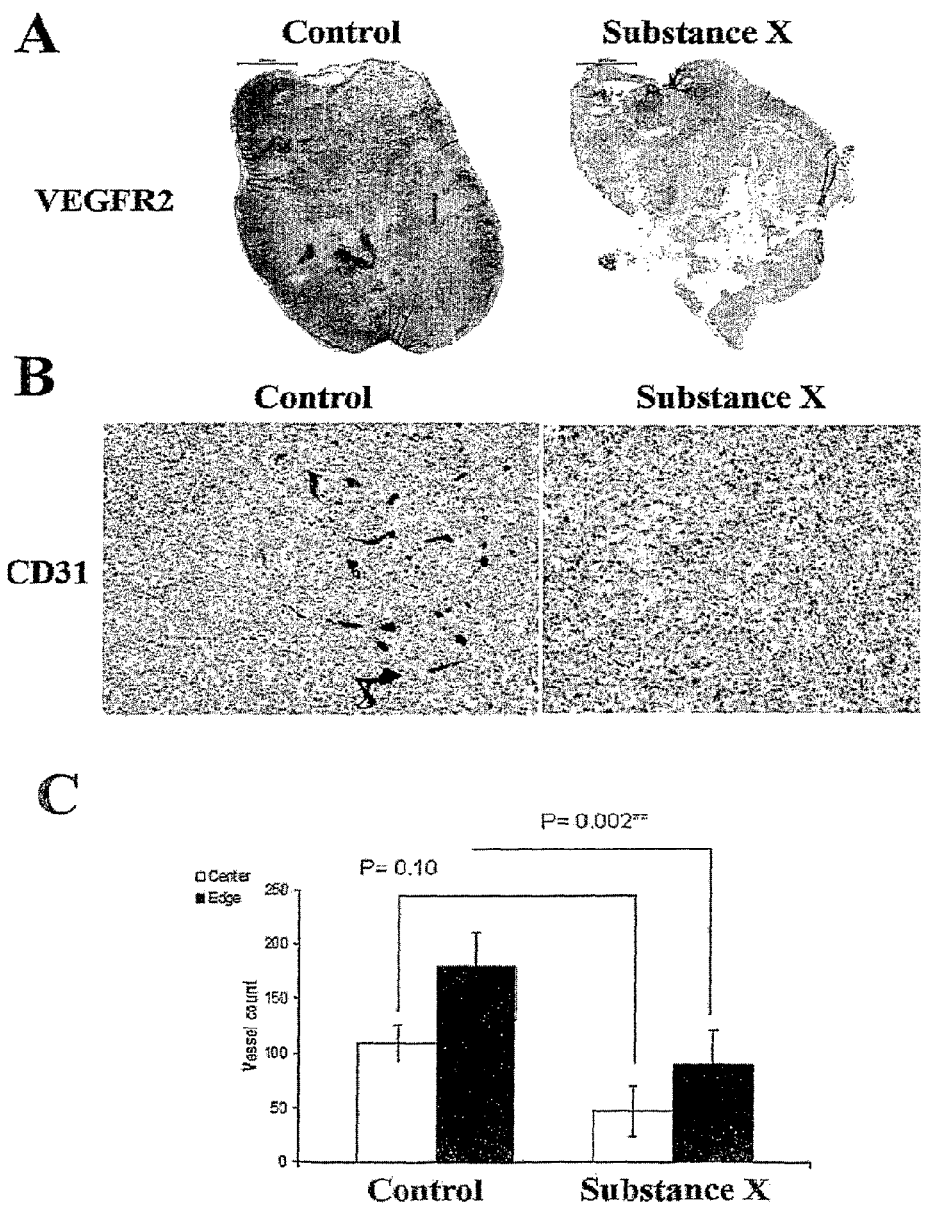
Figure 7:
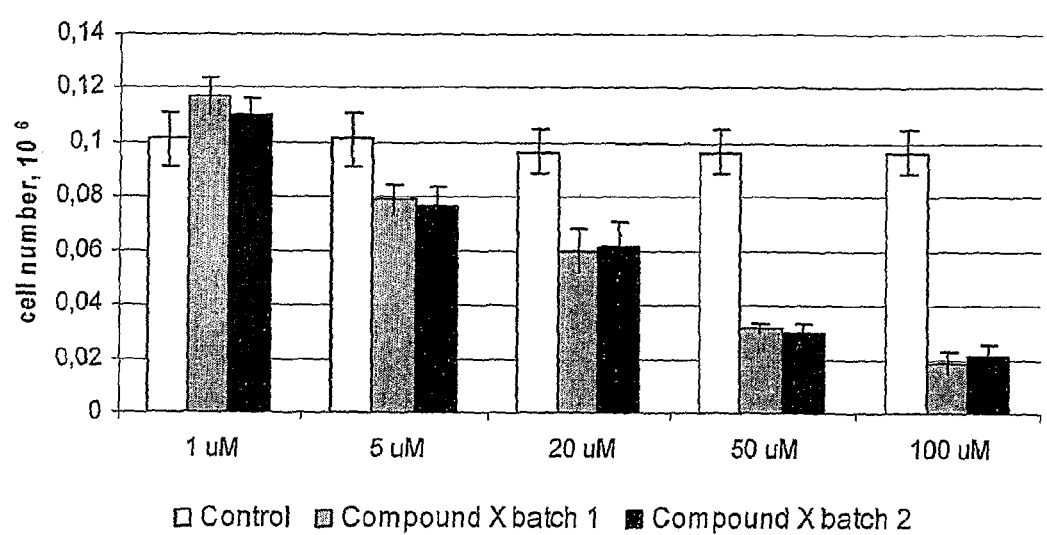
Figure 8:
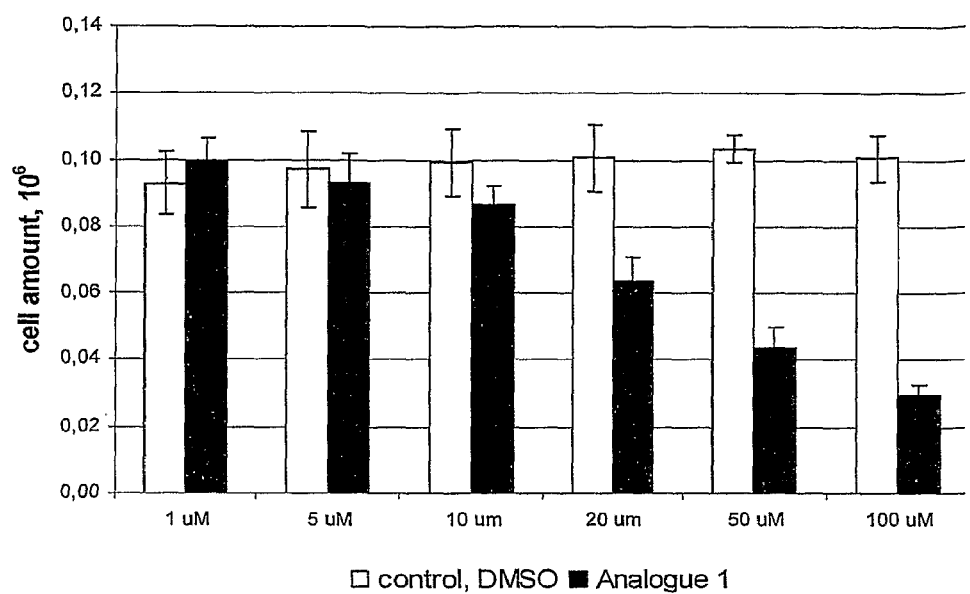
Figure 9:
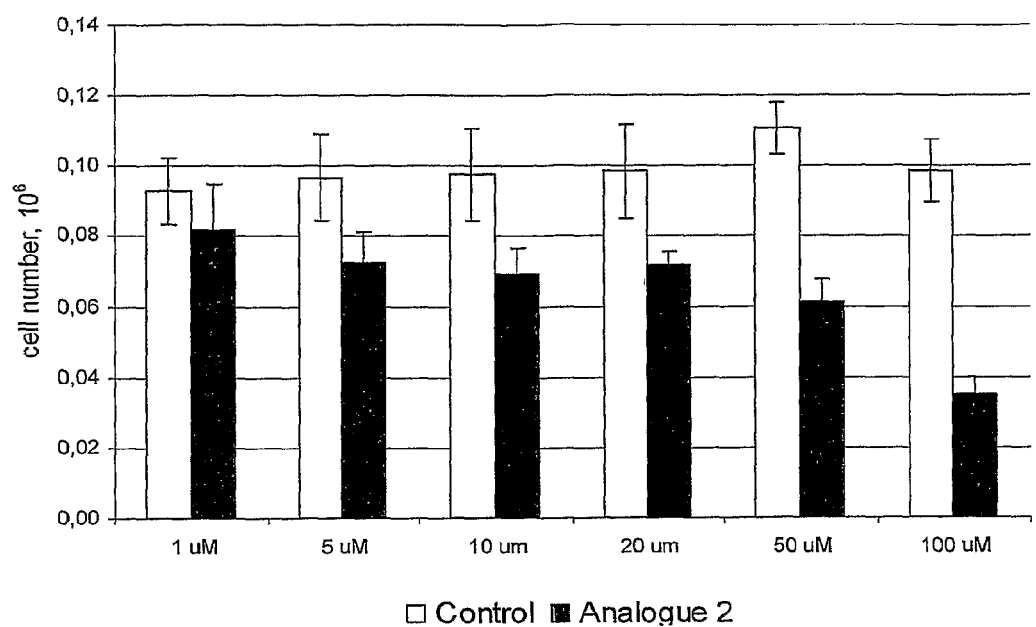
Figure 10:
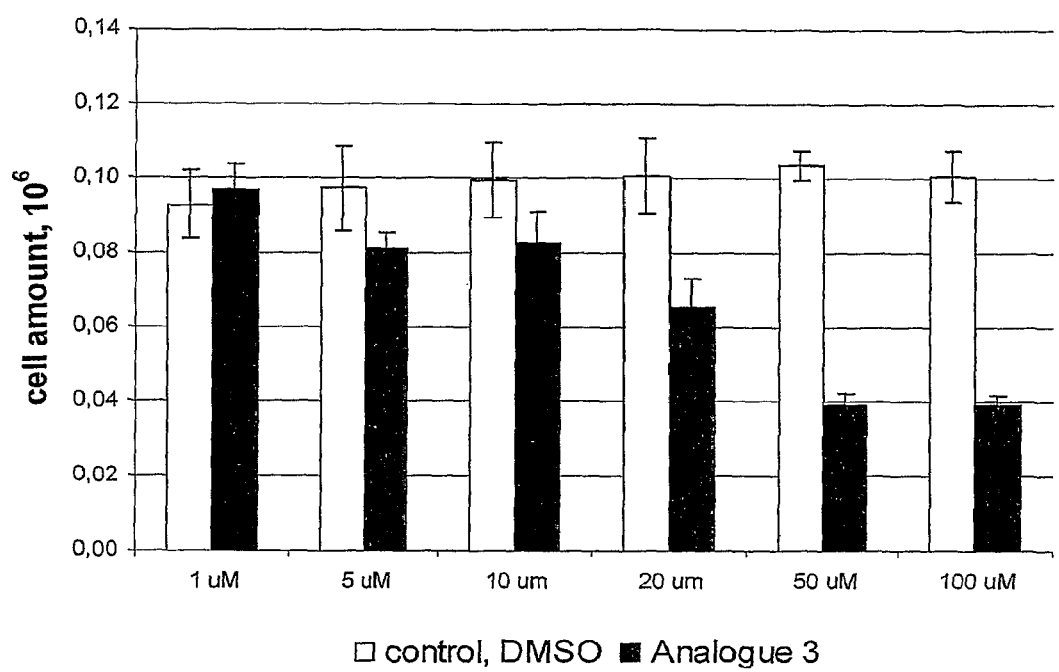
Figure 11:
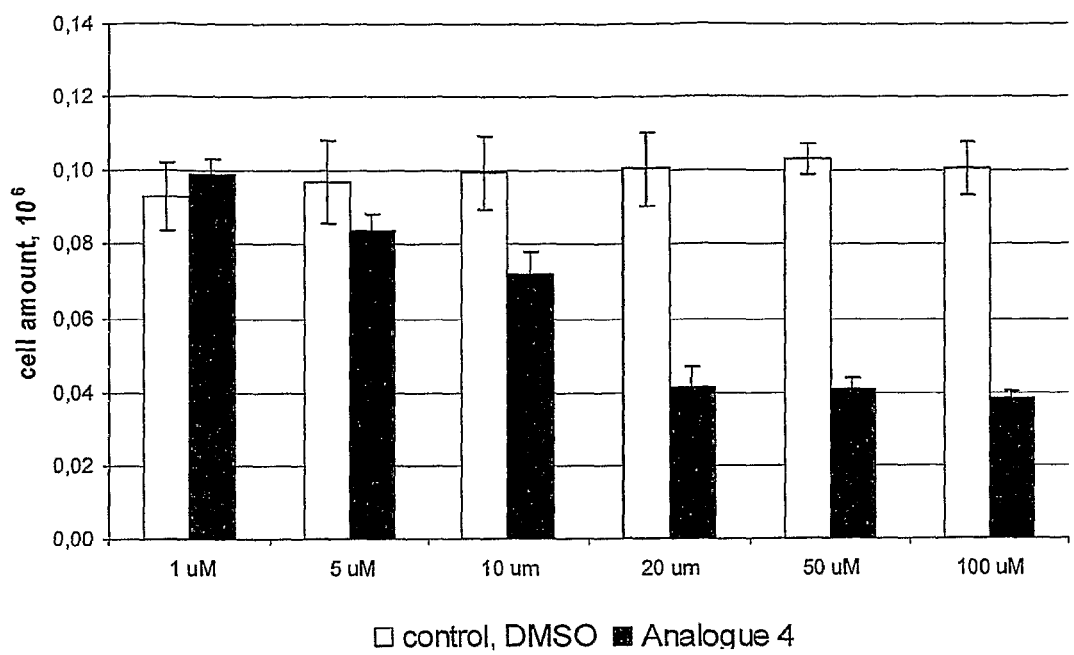
Figure 12:
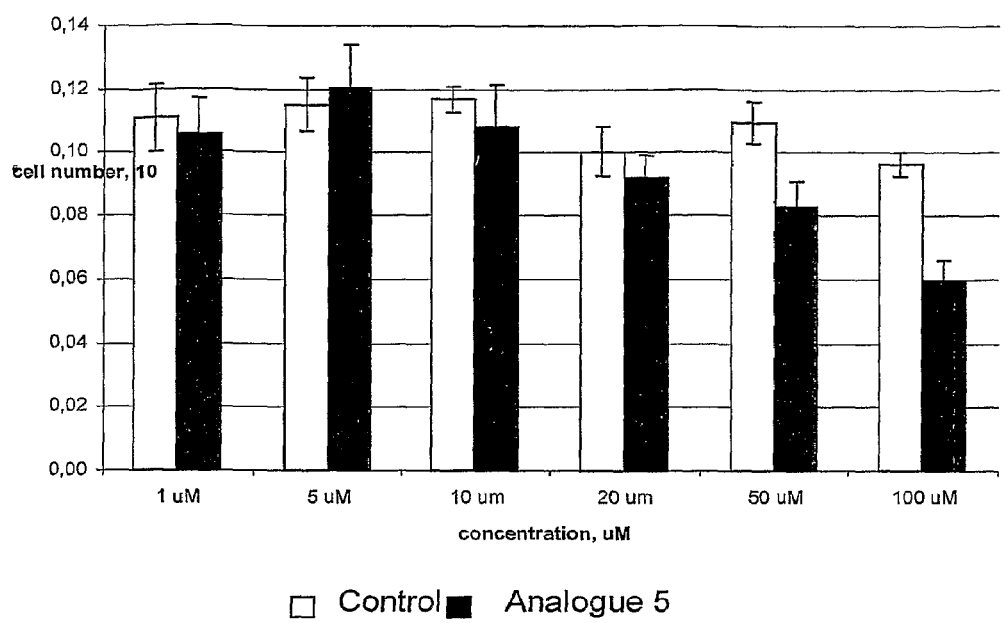
Figure 13:
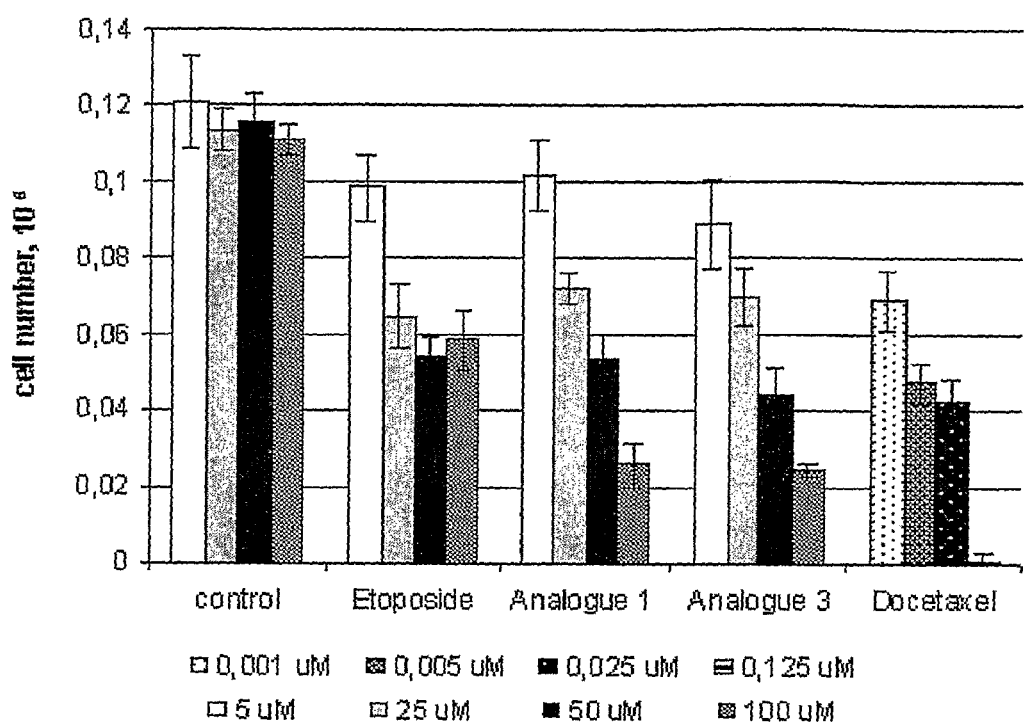
FIG. 13 shows a side by side comparison of the effect of Analogues 1 and 3 with Etoposide and Docetaxel.
Figure 14:
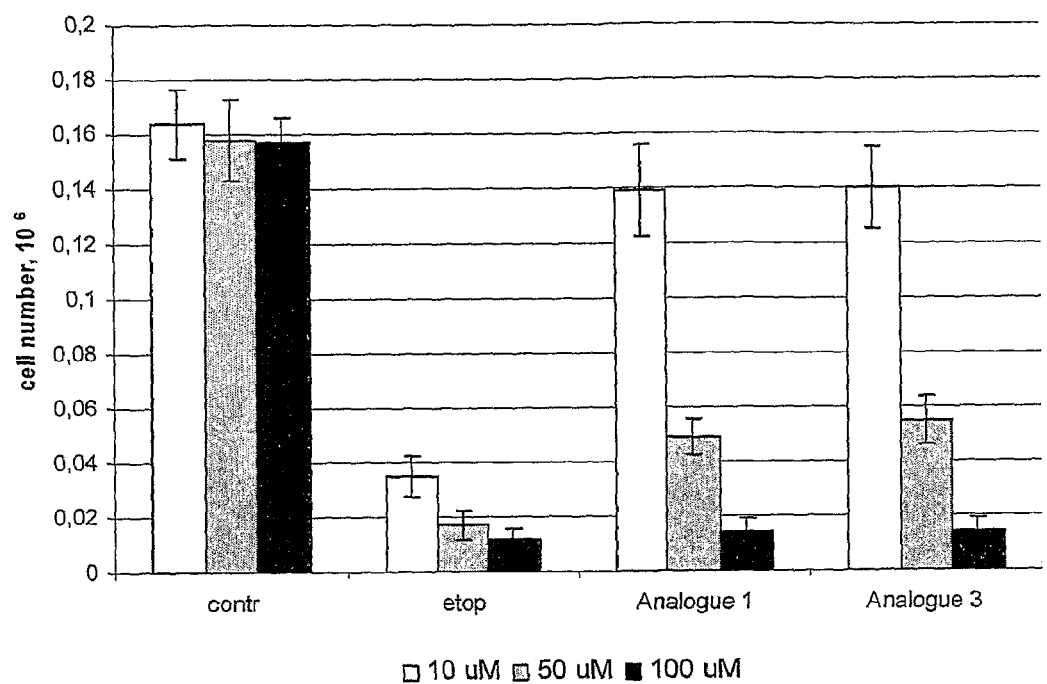
FIG. 14 shows the antitumor effect of Anaolgue 1 and 3 on 0937 human leukemic monocyte lymphoma cell line.
Figure 15:
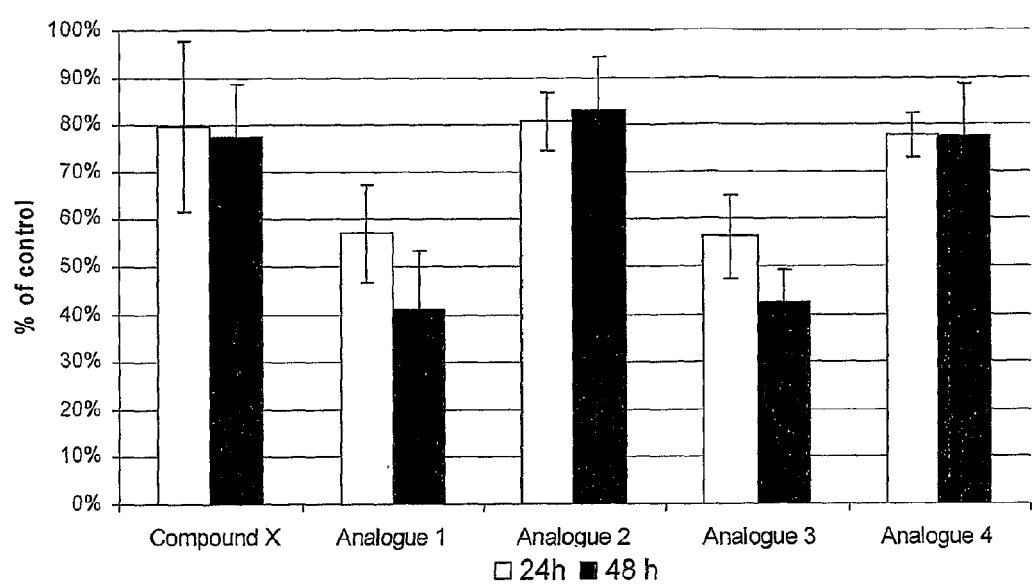
Figure 16:
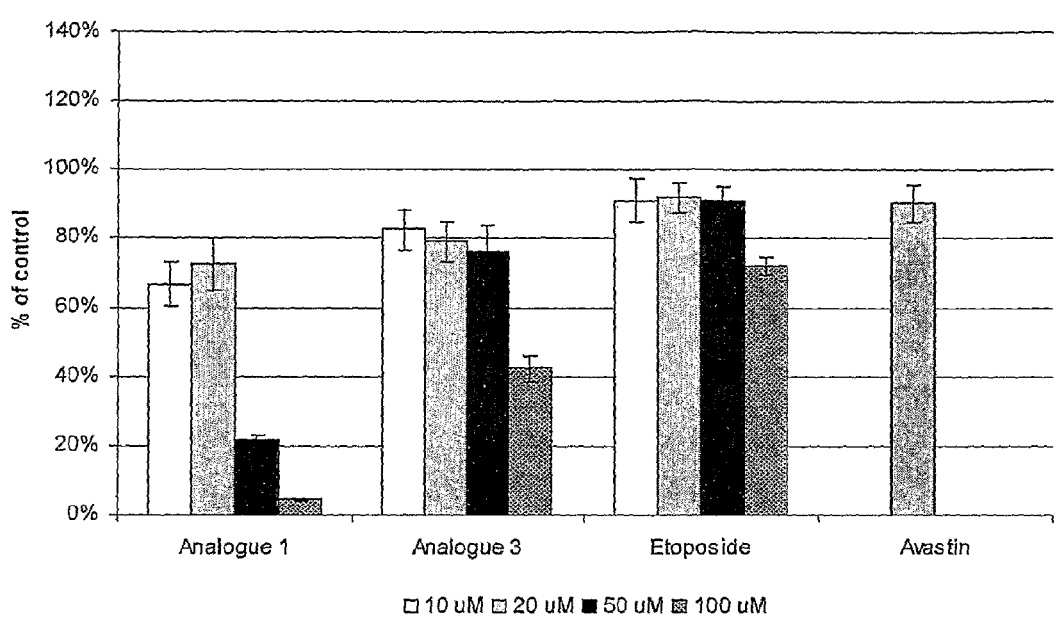
Figure 17:
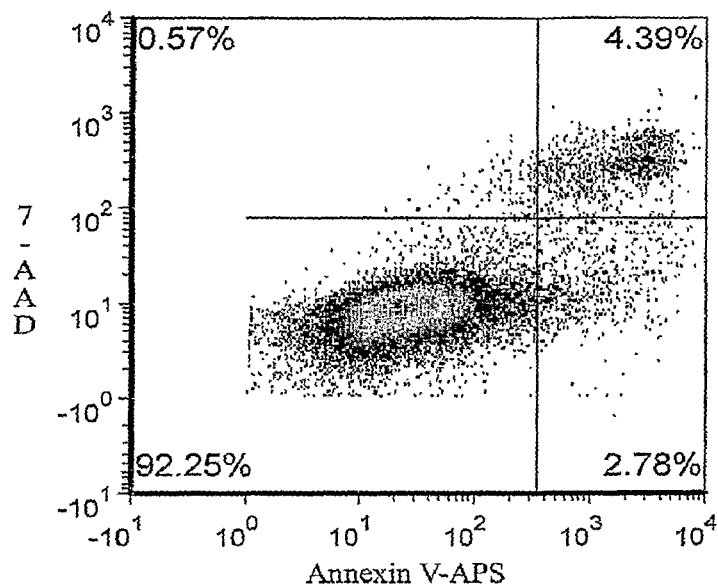
Figure 17:
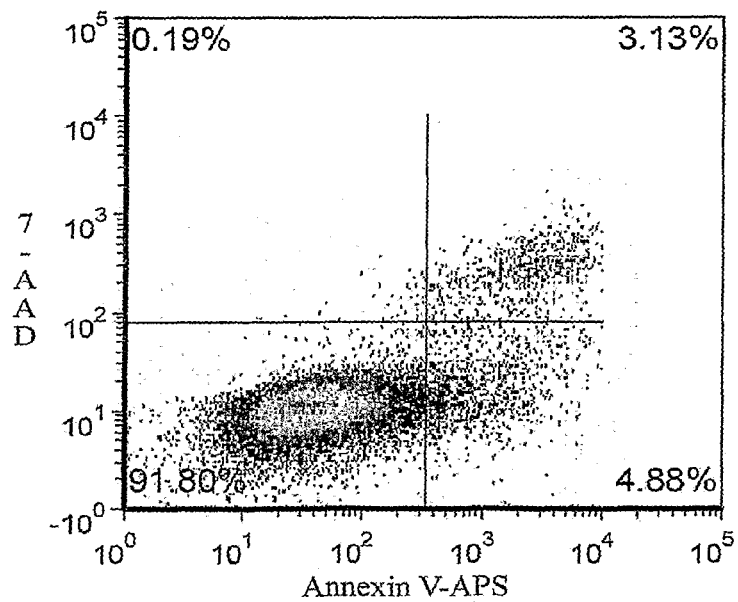
Figure 18:
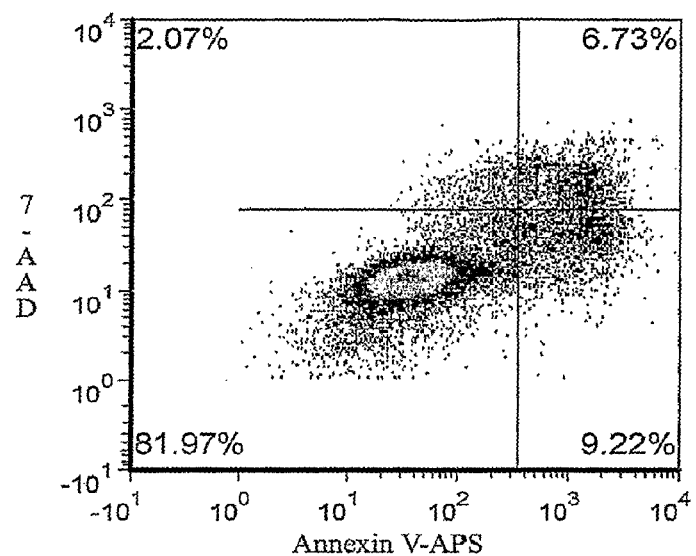
Figure 18:
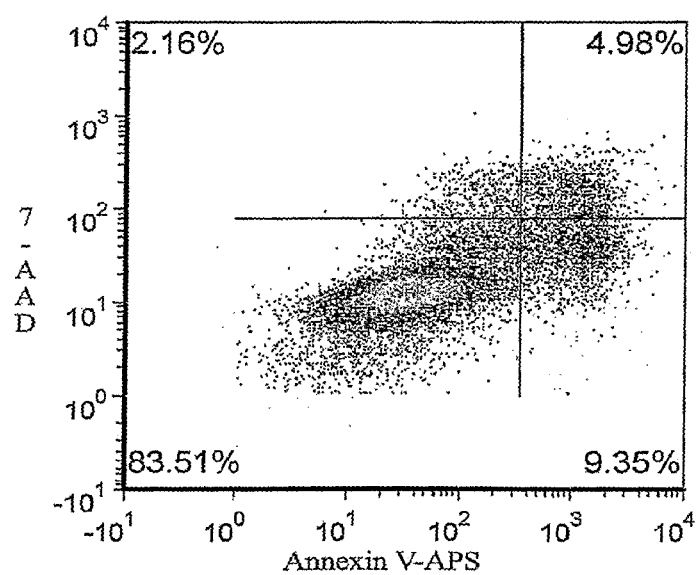
Figure 19:
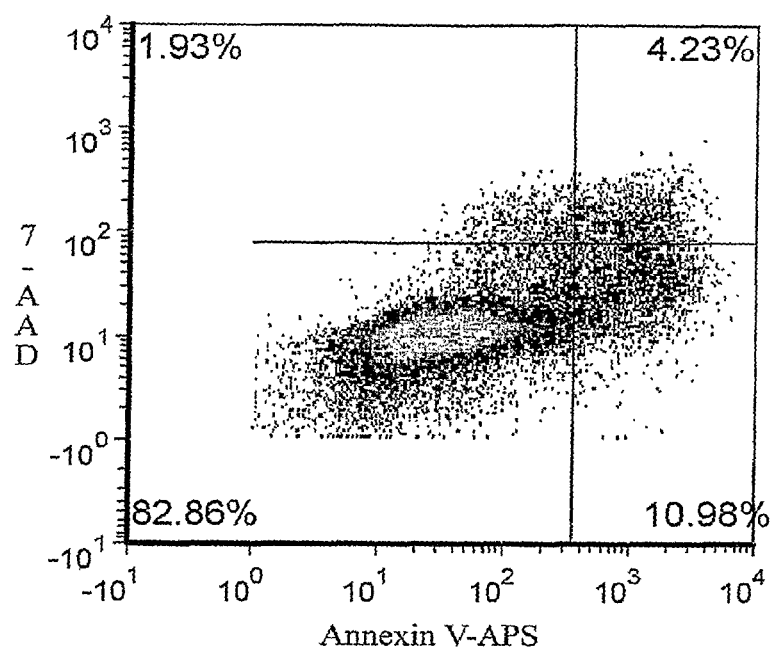
Figure 19:
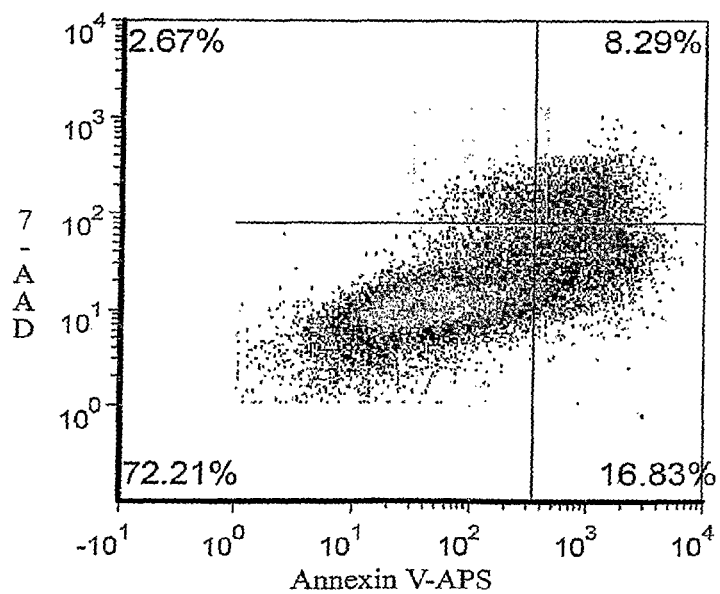
Figure 20:
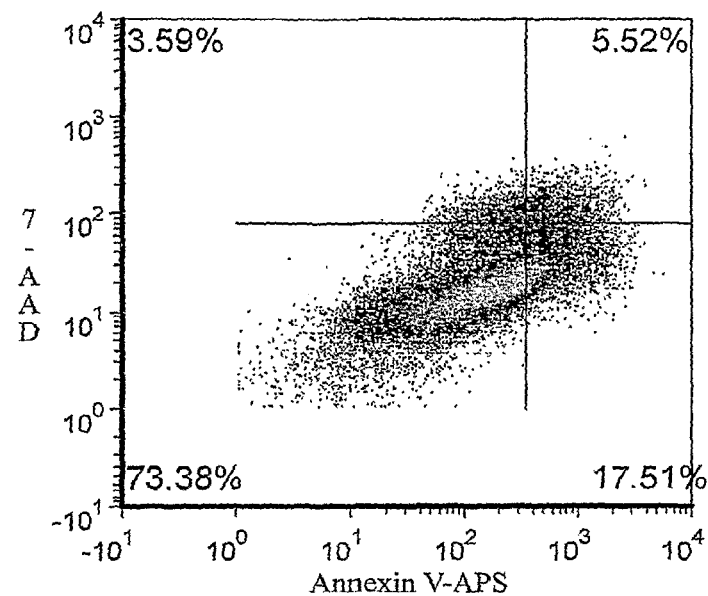
Figure 20:
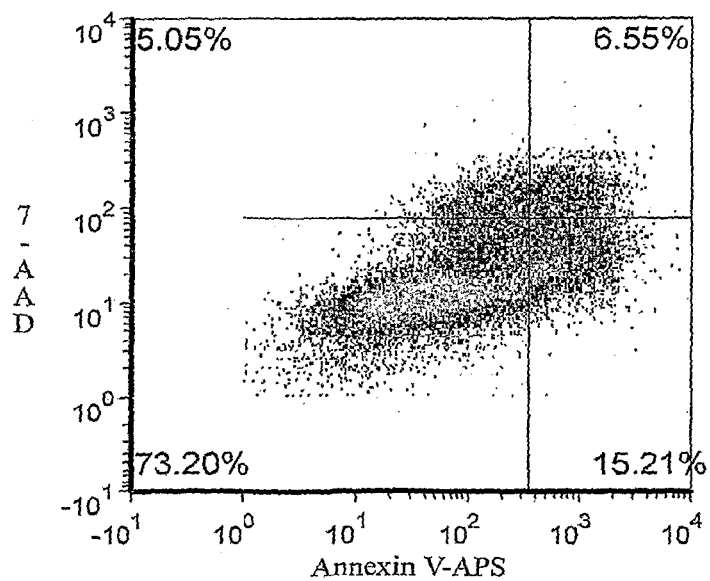
Figure 21:
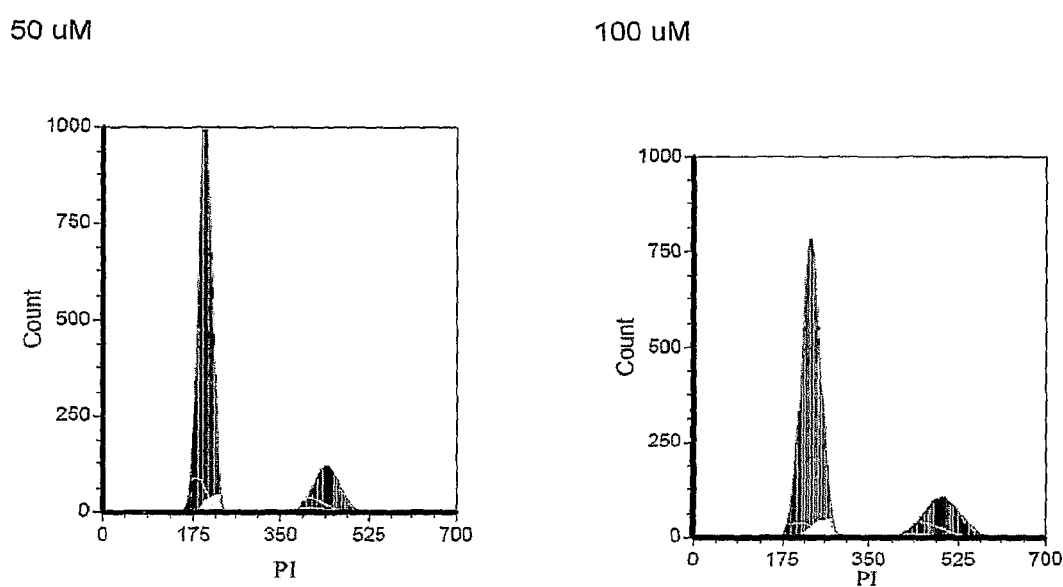
Figure 22:
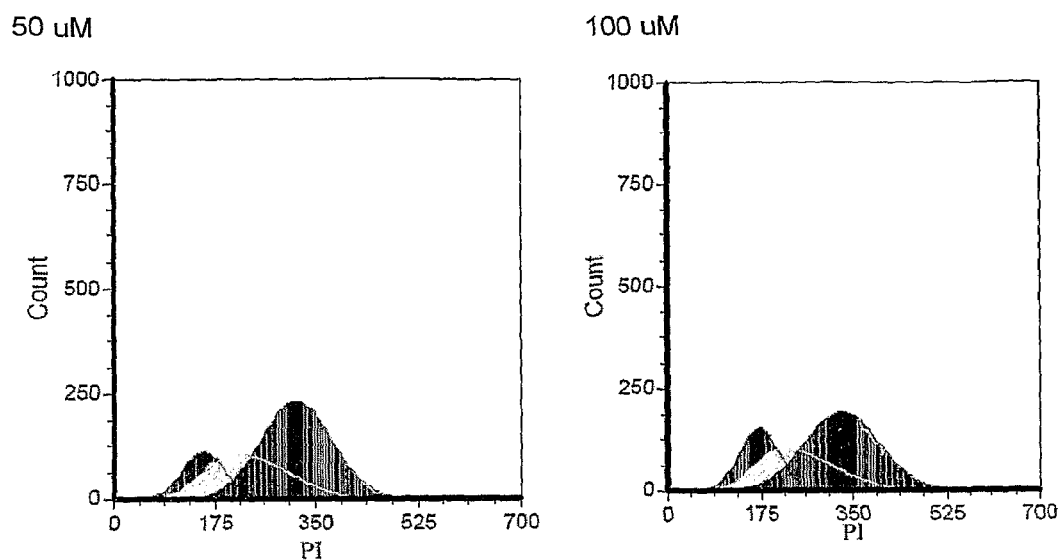
Figure 23:
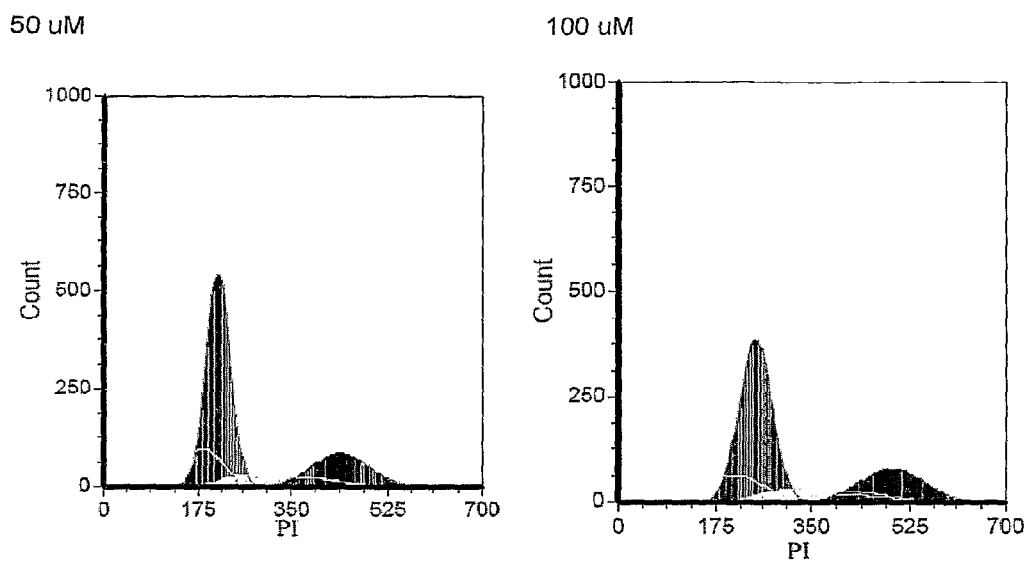
Figure 24:
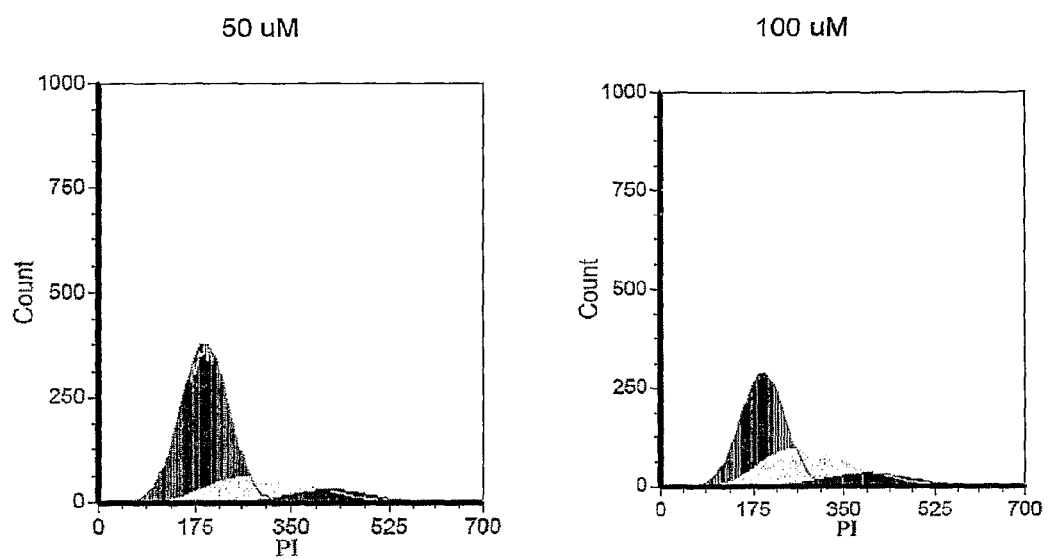

The results are depicted in FIGS. 15 and 16.

Apoptosis Assay

The results are depicted in FIGS. 17, 18, 19 and 20.

|  | control | Etoposide | Analog 1 | Analog 3 |
|---|---|---|---|---|
| 50 uM |  |  |  |  |
| Early apoptosis, % | 2.78 | 9.22 | 10.98 | 15.21 |
| Late apoptosis/necrosis, % | 4.39 | 6.73 | 4.23 | 6.55 |
| Total, % | 7.17 | 15.95 | 15.21 | 21.76 |
| 100 uM |  |  |  |  |
| Early apoptosis, % | 4.88 | 9.35 | 16.83 | 17.51 |
| Late apoptosis/necrosis, % | 3.13 | 4.98 | 8.29 | 5.52 |
| Total, % | 8.01 | 14.33 | 25.12 | 23.03 |

There is increasing in both early and late apoptotic cell number in analogue 1 and analogue 3 treated cells in comparison with control and Etoposide as positive control.

Cell Cycle Analysis

The results are depicted in FIGS. 21, 22, 23 and 24

|  | G0/G1, % | S + G2 + M, % |
|---|---|---|
| 50 uM |  |  |
| control | 65.65 | 34.35 |
| Etoposide | 15.91 | 84.09 |
| Analogue 1 | 63.26 | 36.74 |
| Analogue 3 | 67.52 | 32.48 |
| 100 uM |  |  |
| control | 62.59 | 37.41 |
| Etoposide | 21.39 | 78.61 |
| Analog 1 | 60.44 | 39.56 |
| Analog 3 | 51.77 | 48.23 |

Based on obtained results there was $G_2/M$ phase blockage in Etoposide treated cells, but not in analogue 1 treated cells. There are may be the blockage in cells treated with analogue 3 at 100 uM.

The invention claimed is:

1. A compound of Formula 1;

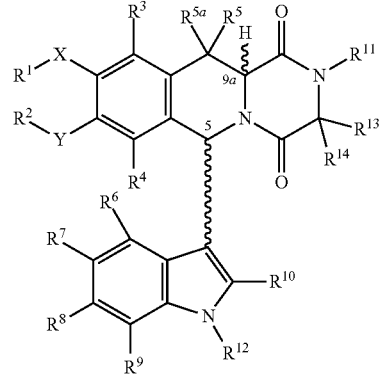

Formula 1 wherein: X and Y are each independently represented by —O—, or —N($R^a$)—;
$R^a$ represents H or $C_{1-6}$ alkyl optionally substituted by one or more fluoro atoms;

wherein ⌇, can have either an R or an S relative configuration, $R^1$ and $R^2$ each independently represent H, $C_{1-6}$ alkyl optionally substituted by one or more fluoro atoms, —C(O)$C_{1-6}$ alkyl optionally substituted by one or more fluoro atoms, or —$CH_2$-phenyl wherein the phenyl is optionally substituted by one or more substituents selected from halo and $C_{1-3}$ alkyl; or $R^1$ and $R^2$ can together represent a $C_{1-2}$ alkylene linker group;

$R^3$, $R^4$, $R^5$, $R^{5a}$, $R^6$, $R^7$, $R^8$, $R^9$, and $R^{10}$ each independently represent H, halo, —$OR^b$, —N($R^c$)$R^d$, $C_{1-6}$ alkyl optionally substituted by one or more fluoro atoms, or —$CH_2$-phenyl wherein the phenyl is optionally substituted by one or more substituents selected from halo and $C_{1-3}$ alkyl; or any two adjacent $R^6$, $R^7$, $R^8$, and $R^9$ groups can be linked together to form a further 3- to 8-membered ring optionally containing one to three double bonds, optionally containing one to four heteroatoms, and wherein the ring is optionally substituted by one or more substituents selected from halo and $C_{1-4}$ alkyl optionally substituted by one or more fluoro atoms;

$R^b$ represents H, $C_{1-6}$ alkyl optionally substituted by one or more fluoro atoms, or —C(O)$C_{1-6}$ alkyl optionally substituted by one or more fluoro atoms;

$R^c$ and $R^d$ each independently represent H or $C_{1-6}$ alkyl optionally substituted by one or more fluoro atoms;

$R^{11}$ and $R^{12}$ each independently represent H, $C_{1-6}$ alkyl optionally substituted by one or more fluoro atoms, —C(O)$C_{1-6}$ alkyl optionally substituted by one or more fluoro atoms, phenyl optionally substituted by one or more substituents selected from halo and $C_{1-3}$ alkyl, or —CH$_2$-phenyl wherein the phenyl is optionally substituted by one or more substituents selected from halo and $C_{1-3}$ alkyl;

$R^{13}$ and $R^{14}$ each independently represent H, $C_{1-6}$ alkyl optionally substituted by one or more fluoro atoms, or —CH$_2$-phenyl wherein the phenyl is optionally substituted by one or more substituents selected from halo and $C_{1-3}$ alkyl, or a pharmaceutically-acceptable salt, ester, stereoisomer or tautomer thereof.

2. The compound of claim 1, further represented by Formula 1A or Formula 1B;

Formula 1A

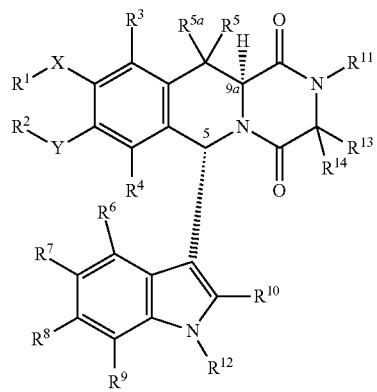

Formula 1B

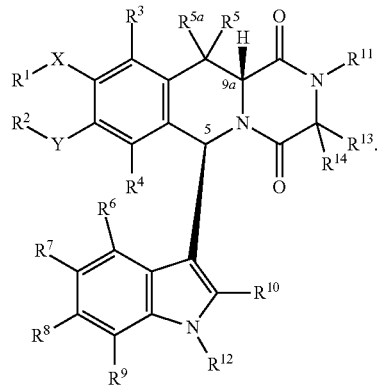

3. The compound of claim 2, wherein the compound is represented by:

Formula 2B

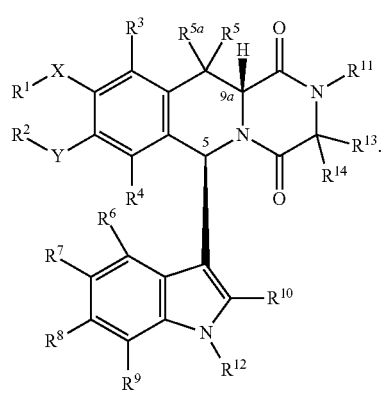

4. The compound of claim 3, wherein $R^1$ and $R^2$ independently represent H, unsubstituted $C_{1-6}$ alkyl, unsubstituted —C(O)$C_{1-6}$ alkyl, or unsubstituted —CH$_2$-phenyl; or $R^1$ and $R^2$ may together represent a $C_{1-2}$ alkylene linker group.

5. The compound of claim 3, wherein $R^3$, $R^4$, $R^5$, $R^{5a}$, $R^6$, $R^7$, $R^8$, $R^9$, and $R^{10}$ independently represent H, halo, —OR$^b$, unsubstituted $C_{1-6}$ alkyl, or unsubstituted —CH$_2$-phenyl.

6. The compound of claim 3, wherein R$^b$ represents H or unsubstituted $C_{1-6}$ alkyl, and R$^c$ and R$^d$ independently represent H or unsubstituted $C_{1-6}$ alkyl; or wherein R$^b$ represents H or unsubstituted $C_{1-6}$ alkyl, or R$^c$ and R$^d$ independently represent H or unsubstituted $C_{1-6}$ alkyl.

7. The compound of claim 3, wherein $R^{11}$ and $R^{12}$ independently represent H, unsubstituted $C_{1-6}$ alkyl, or unsubstituted phenyl, and $R^{13}$ and $R^{14}$ independently represent H or unsubstituted $C_{1-6}$ alkyl; or wherein $R^{11}$ and $R^{12}$ independently represent H, unsubstituted $C_{1-6}$ alkyl, or unsubstituted phenyl, or $R^{13}$ and $R^{14}$ independently represent H or unsubstituted $C_{1-6}$ alkyl.

8. The compound of claim 3, wherein $R^7$ is Cl.

9. The compound of claim 3, wherein $R^{11}$ is —CH$_3$.

10. The compound of claim 3, wherein $R^7$ is —O—CH$_3$.

11. A method of modulating vascular endothelial growth factor kinase activity in a subject, the method comprising the administering to said subject of a therapeutically effective amount of a compound of claim 3, or a pharmaceutically-acceptable salt, ester, stereoisomer, or tautomer thereof.

12. The method of claim 11, wherein the subject has a cancer selected from the group consisting of hepatocellular adenoma, focal nodular hyperplasia, acoustic neuroma, a neurofibroma, bile duct adenoma, bile duct cystadenoma, a fibroma, a lipoma, a leiomyoma, a mesothelioma, a teratoma, a myxoma, nodular regenerative hyperplasia, trachoma, a leukemia, a myelodysplastic syndrome, prostate cancer, breast cancer, a skin cancer, a bone cancer, liver cancer, lung cancer, brain cancer, cancer of the larynx, bladder cancer, gall bladder, ovary cancer, cervical cancer, pancreatic cancer, rectal cancer, parathyroid cancer, thyroid cancer, esophageal cancer, adrenal cancer, a neural tissue cancer, head and neck cancer, colon cancer, stomach cancer, bronchial cancer, kidney cancer, basal cell carcinoma, squamous cell carcinoma of both ulcerating and papillary type, metastatic skin carcinoma, osteosarcoma, Ewing's sarcoma, reticulum cell sarcoma, myeloma, giant cell tumor, small-cell lung tumor, non-small cell lung tumor, islet cell tumor, primary brain tumor, acute and chronic lymphocytic and granulocytic tumors, hairy-cell tumor, an adenoma, a hyperplasia, medullary carcinoma, pheochromocytoma, mucosal neuromas, intestinal ganglioneuroma, hyperplastic corneal nerve tumor, marfanoid habitus tumor, Wilm's tumor, a seminoma, ovarian tumor, leiomyomata tumor, cervical dysplasia and in situ carcinoma, neuroblastoma, retinoblastoma, soft tissue sarcoma, malignant carcinoid, topical skin lesion, mycosis fungoides, rhabdomyosarcoma, Kaposi's sarcoma, osteogenic and other sarcoma, renal cell tumor, polycythemia vera, an adenocarcinoma, glioblastoma multiforme, a lymphoma, malignant melanoma, epidermoid carcinoma, and other carcinomas and sarcomas.

13. The method of claim 11, wherein the subject is a mammal.

14. The method of claim 11, wherein the administration is oral, intravenous, subcutaneous, buccal, rectal, dermal, nasal, tracheal, bronchial, or sublingual.

15. The method of claim 11, wherein between 0.01 mg to 10 g of the compound is administered daily.

16. The method of claim 11, wherein between 1 mg/kg to 1000 mg/kg of the compound is administered daily.

17. A pharmaceutical formulation including a compound of claim 1, or a pharmaceutically-acceptable salt, ester, stereoisomer, or tautomer thereof, in an admixture with a pharmaceutically-acceptable adjuvant, diluent, or carrier.

18. A pharmaceutical composition comprising:
(A) a compound of claim 1; and
(B) one or more therapeutic agents,
wherein each of components (A) and (B) is formulated separately or in an admixture with a pharmaceutically-acceptable adjuvant, diluent, or carrier.

19. A process for the preparation of a compound of claim 1 comprising one of the following methods:
(i) a method comprising reacting a compound of Formula 1B in which $R^1$ and $R^2$ both represent hydrogen, with a compound of Formula II, $$L^1\text{-}R^{1/2}\text{-}L^2 \qquad \text{II}$$

wherein $L^1$ and $L^2$ independently represent leaving groups selected from a sulfonate group, chloro, bromo, or iodo, and $R^{1/2}$ represents $C_{1-2}$ alkylene;

(ii) a method comprising
a) reacting a compound of Formula III,

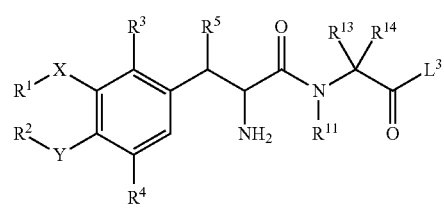

III or single enantiomer thereof, wherein $L^3$ represents a leaving group selected from a sulfonate group, chloro, bromo, or iodo, with a compound of Formula IV,

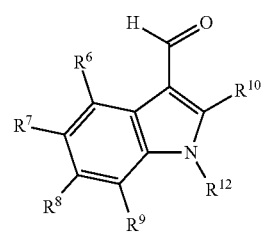

IV to produce a compound of Formula V; and
b) intramolecularly cyclizing the compound of Formula V,

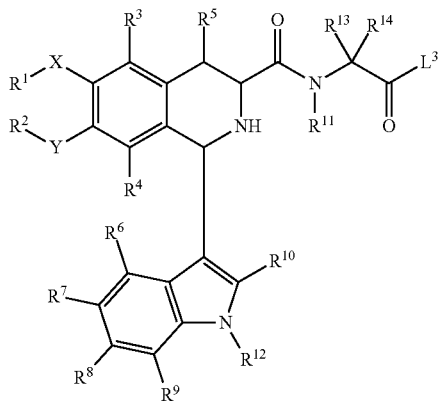

V or a single diastereomer thereof, or a pharmaceutically-acceptable salt thereof to produce compounds of Formula 1B; and (iii) a method comprising reacting a corresponding compound of Formula 1B in which $R^{11}$ and/or $R^{12}$ represents hydrogen, with a compound of (or two different compounds of) Formula VI, $$R^{11/12}\text{-}L^4 \qquad \text{VI}$$

wherein $R^{11/12}$ represents $R^{11}$ or $R^{12}$ as defined in claim 1, provided that it does not represent hydrogen; and $L^4$ represents a leaving group selected from a sulfonate group, chloro, bromo, or iodo.

20. A process for the preparation of a pharmaceutical formulation of claim 17 comprising bringing into association a compound of Formula 1B, or a pharmaceutically-acceptable salt, ester, stereoisomer, or tautomer thereof with a pharmaceutically-acceptable adjuvant, diluent, or carrier.

21. A process for the preparation of the pharmaceutical composition of claim 18 comprising bringing a compound of Formula 1B, or a pharmaceutically acceptable salt, ester, stereoisomer or tautomer thereof, into association with the one or more therapeutic agents and at least one pharmaceutically-acceptable adjuvant, diluent or carrier.

\* \* \* \* \*